(12) United States Patent
Whitmore, III et al.

(10) Patent No.: US 7,909,815 B2
(45) Date of Patent: Mar. 22, 2011

(54) INSTRUMENT GUIDE FOR USE WITH NEEDLES AND CATHETERS

(75) Inventors: Willet Francis Whitmore, III, Long Boat Key, FL (US); Craig Joseph Cermak, Riverside, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 875 days.

(21) Appl. No.: 10/961,936

(22) Filed: Oct. 8, 2004

(65) Prior Publication Data

US 2005/0143753 A1 Jun. 30, 2005

Related U.S. Application Data

(63) Continuation-in-part of application No. 10/851,030, filed on May 21, 2004, now abandoned.

(60) Provisional application No. 60/472,749, filed on May 23, 2003.

(51) Int. Cl.
*A61B 17/00* (2006.01)
(52) U.S. Cl. .......................................... 606/1
(58) Field of Classification Search .................. 600/407, 600/409, 437, 461–471, 564–572, 562, 581, 600/576–579; 606/1
See application file for complete search history.

(56) References Cited

U.S. PATENT DOCUMENTS

| | | | |
|---|---|---|---|
| 4,108,165 A | 8/1978 | Kopp et al. | 128/2 V |
| 4,363,326 A | 12/1982 | Kopel | 128/660 |
| 4,402,324 A | 9/1983 | Lindgren et al. | 128/660 |
| 4,469,106 A | 9/1984 | Harui | 128/660 |
| 4,489,730 A | 12/1984 | Jingu | 128/660 |
| 4,497,325 A | 2/1985 | Wedel | 128/754 |
| 4,542,747 A | 9/1985 | Zurinski et al. | 128/660 |
| 4,635,644 A | 1/1987 | Yagata | 128/660 |
| 4,733,661 A | 3/1988 | Palestrant | 128/303 B |
| 4,742,829 A | 5/1988 | Law et al. | 128/660 |
| 4,877,033 A | 10/1989 | Seitz, Jr. | 128/660.05 |
| 4,898,178 A | 2/1990 | Wedel | 128/662.05 |
| 4,899,756 A | 2/1990 | Sonek | 128/662.05 |
| 4,911,173 A | 3/1990 | Terwilliger | 128/662.06 |
| 5,031,634 A | 7/1991 | Simon | 128/754 |

(Continued)

FOREIGN PATENT DOCUMENTS

JP 2-13439 1/1990

(Continued)

OTHER PUBLICATIONS

CIVCO Medical Instruments Co., Inc. Transducer Covers. Biopsy Needle Guides. GE Medical Systems Imaging Accessories—vol. 1, pp. cover, 2-3, back cover, dated 2003.

(Continued)

*Primary Examiner* — Ahmed M Farah
*Assistant Examiner* — Aaron Roane
(74) *Attorney, Agent, or Firm* — Caesar, Rivise, Bernstein, Cohen & Pokotilow, Ltd.

(57) ABSTRACT

A guide is provided for use with an imaging instrument, the guide including a first portion, a second portion proximate the first portion, and a cavity at least partially formed by the first and second portions, the cavity having a cavity width and configured to retain an instrument therein. The cavity width is selectively changeable to accommodate a plurality of diameters by sliding the second portion along a path with respect to the first portion.

38 Claims, 17 Drawing Sheets

U.S. PATENT DOCUMENTS

| | | | | |
|---|---|---|---|---|
| 5,052,396 | A | 10/1991 | Wedel et al. | 128/662.05 |
| 5,076,279 | A * | 12/1991 | Arenson et al. | 600/461 |
| 5,100,387 | A | 3/1992 | Ng | 604/116 |
| 5,196,019 | A | 3/1993 | Davis et al. | 606/130 |
| 5,235,987 | A | 8/1993 | Wolfe | 128/662.05 |
| 5,343,865 | A | 9/1994 | Gardineer et al. | 128/662.05 |
| 5,469,853 | A | 11/1995 | Law et al. | 128/662.06 |
| 5,494,039 | A | 2/1996 | Onik et al. | 128/662.05 |
| 5,623,931 | A | 4/1997 | Wung et al. | 128/662.05 |
| 5,682,892 | A | 11/1997 | Selder et al. | 128/653.2 |
| 5,758,650 | A | 6/1998 | Miller et al. | 128/662.05 |
| 5,924,992 | A | 7/1999 | Park et al. | 600/461 |
| 5,941,889 | A | 8/1999 | Cermak | 606/130 |
| 6,095,981 | A | 8/2000 | McGahan | 600/461 |
| 6,203,499 | B1 | 3/2001 | Imling et al. | 600/461 |
| 6,296,614 | B1 | 10/2001 | Pruter | 600/461 |
| 6,361,499 | B1 | 3/2002 | Bates et al. | 600/461 |
| 6,368,280 | B1 | 4/2002 | Cermak et al. | 600/459 |
| 6,475,152 | B1 | 11/2002 | Kelly, Jr. et al. | 600/461 |
| 6,494,844 | B1 | 12/2002 | Van Bladel et al. | 600/567 |
| 6,592,559 | B1 | 7/2003 | Pakter et al. | 604/272 |
| 6,604,944 | B2 * | 8/2003 | Swan | 433/88 |
| 6,758,817 | B1 | 7/2004 | Pruter et al. | 600/461 |
| 6,814,704 | B2 * | 11/2004 | Weilandt | 600/461 |
| 2005/0113816 | A1 | 5/2005 | Whitmore, III et al. | 606/23 |

FOREIGN PATENT DOCUMENTS

| | | |
|---|---|---|
| WO | WO 84/03034 | 8/1984 |

OTHER PUBLICATIONS

CIVCO Medical Instruments Co., Inc. Transducer Covers. Biopsy Needle Guides. ACUSON & SONOLINE Imaging Accessories—vol. 1, pp. cover, 2-3, back cover, dated 2003.

CIVCO Medical Instruments Imaging Supplies vol. 1, pp. cover, 1, 5-7, 15-23, back cover, dated 2003.

Brandy R. Schroeder, "On Target: Ultrasound Navigates the Way," PROGRAM, published by CIVCO Medical Instruments Co., Inc., Winter 2001, pp. cover, 4-5.

AMEDIC PathFinder®, 19 printed pages posted at http://www.amedic.se/pathfinder/.

Supplemental Declaration of Rick L. Pruter, with Exhibits, dated Nov. 18, 2004, submitted in *CIVCO Medical Instruments Co., Inc. v. Protek Medical Products, Inc.*, United States District Court, Southern District of Iowa, Central Division, No. 4:03-CV-40722.

Protek Medical Products, Inc., Ultrasound & Imaging Accessories, Needle Guides, Director™, 3 printed pages, posted at http://www.protekmedical.com/pages/needleguides.html#Anchor-Director-49575, dated 2003.

* cited by examiner

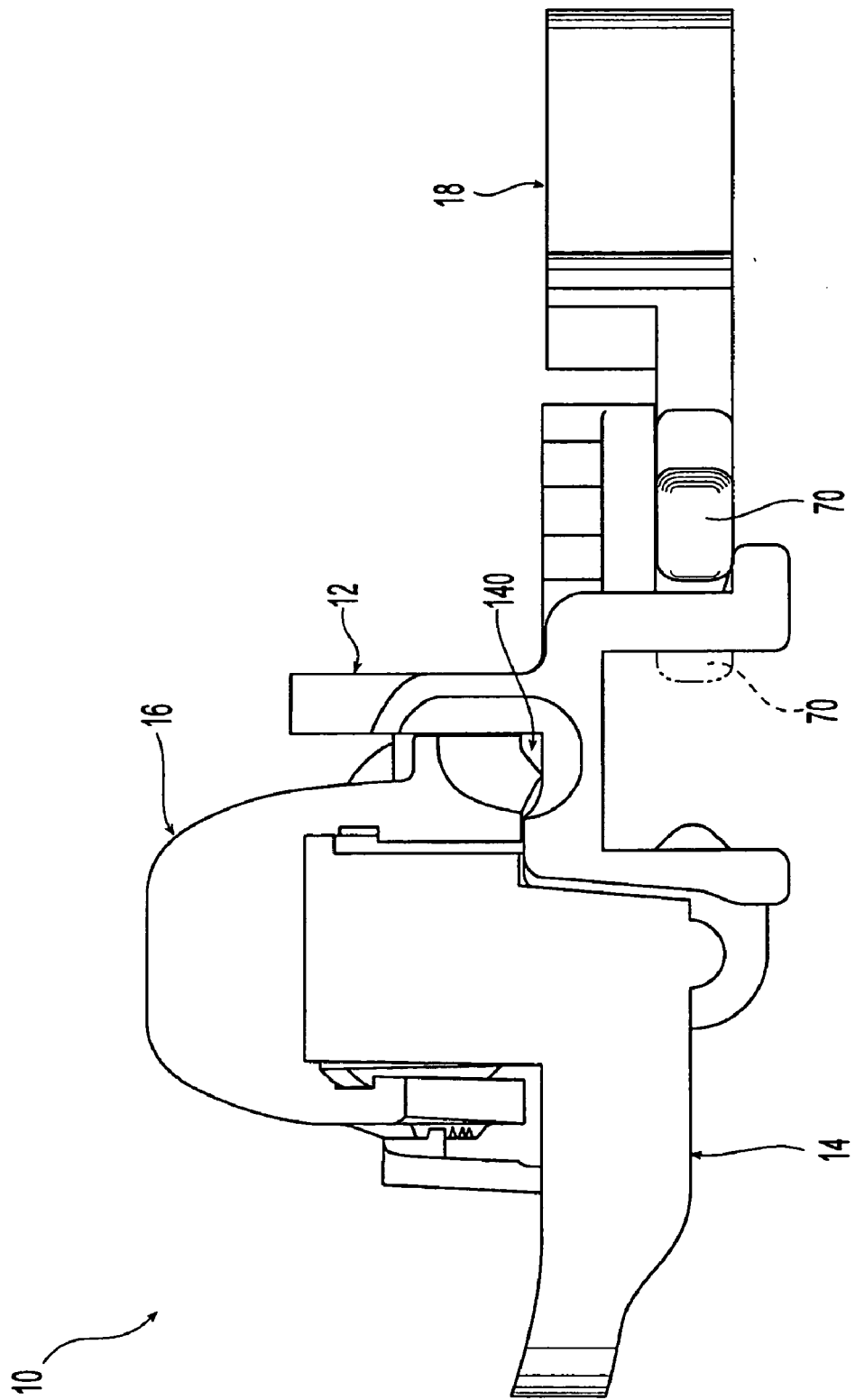

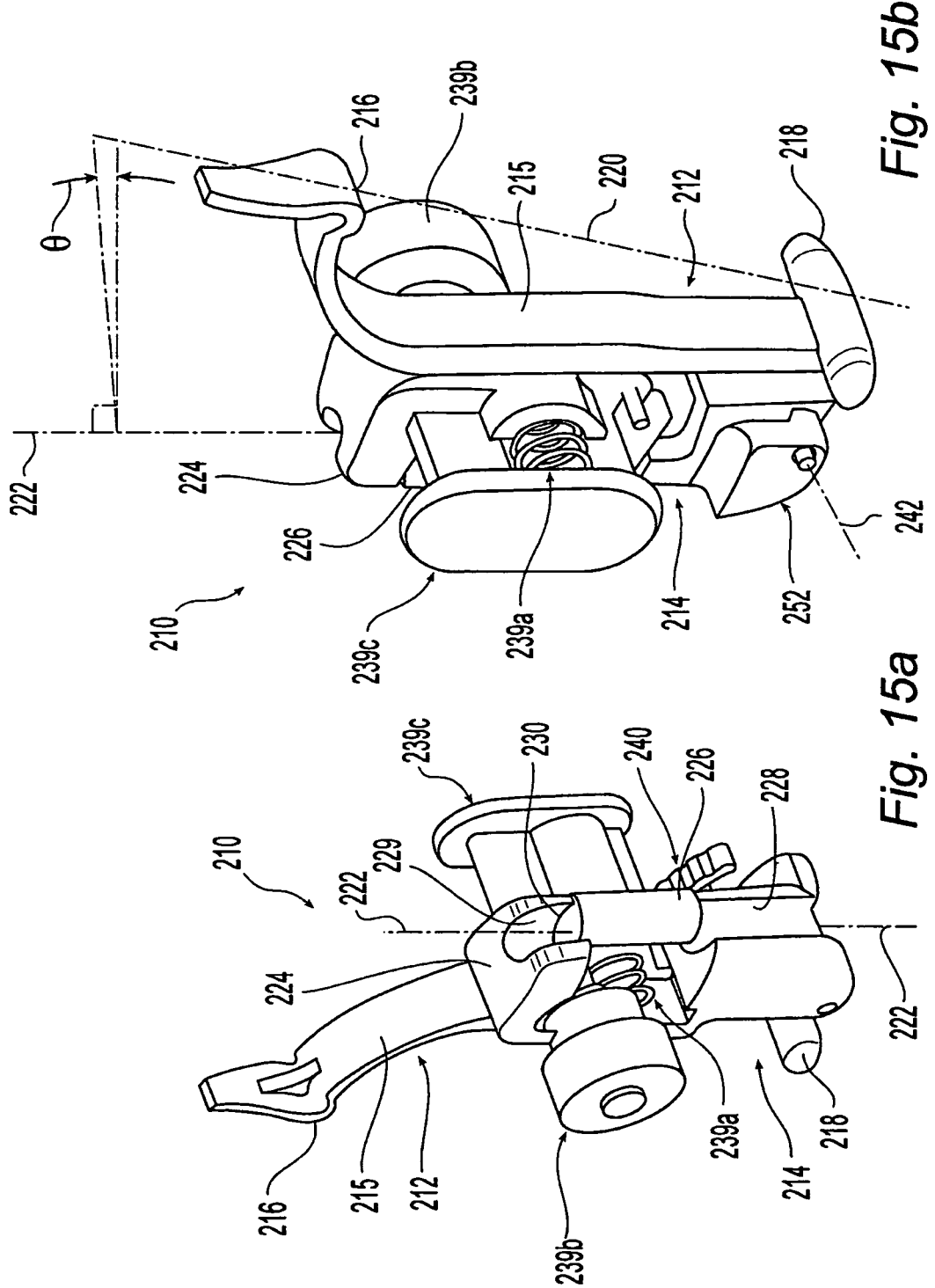

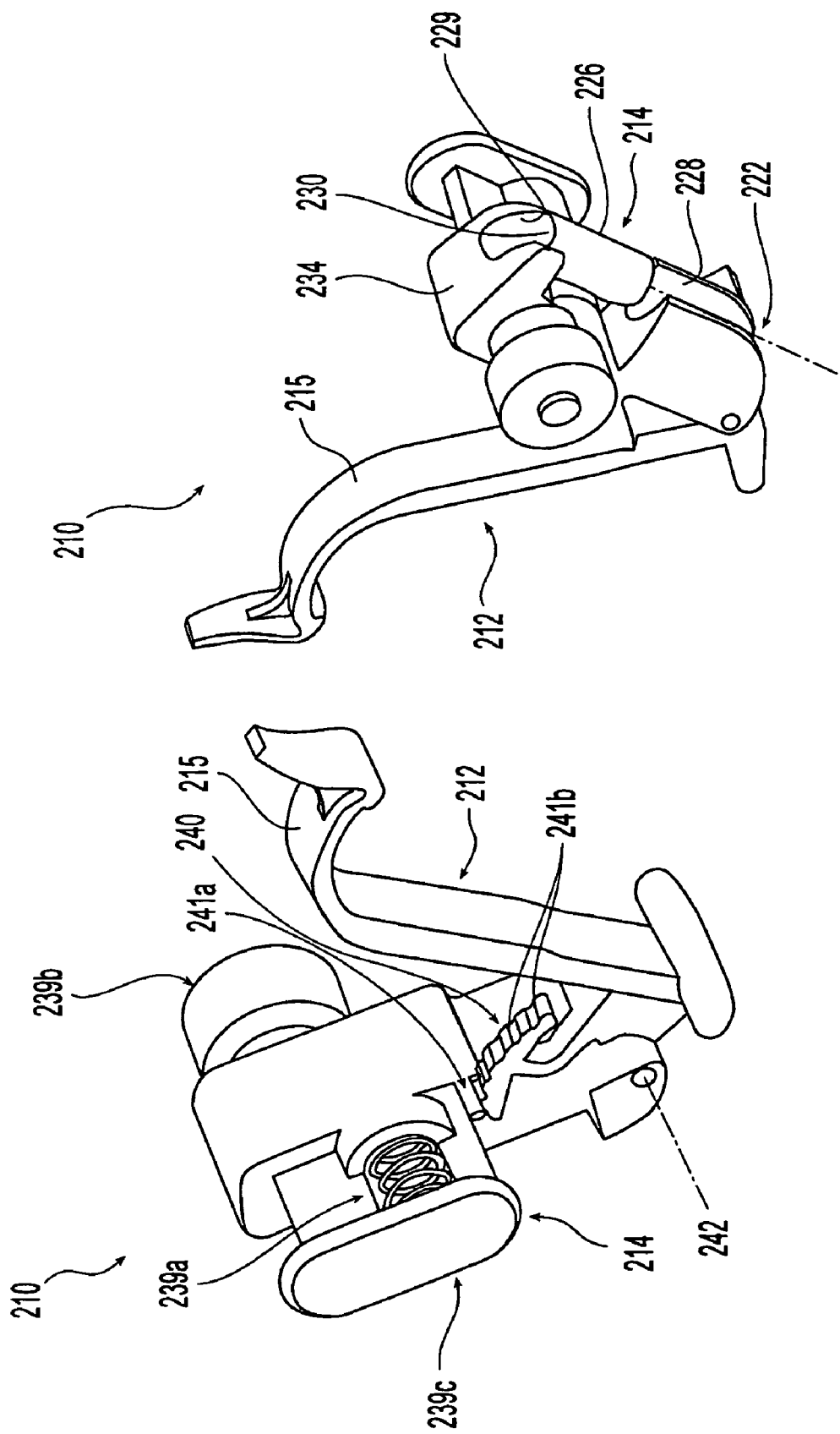

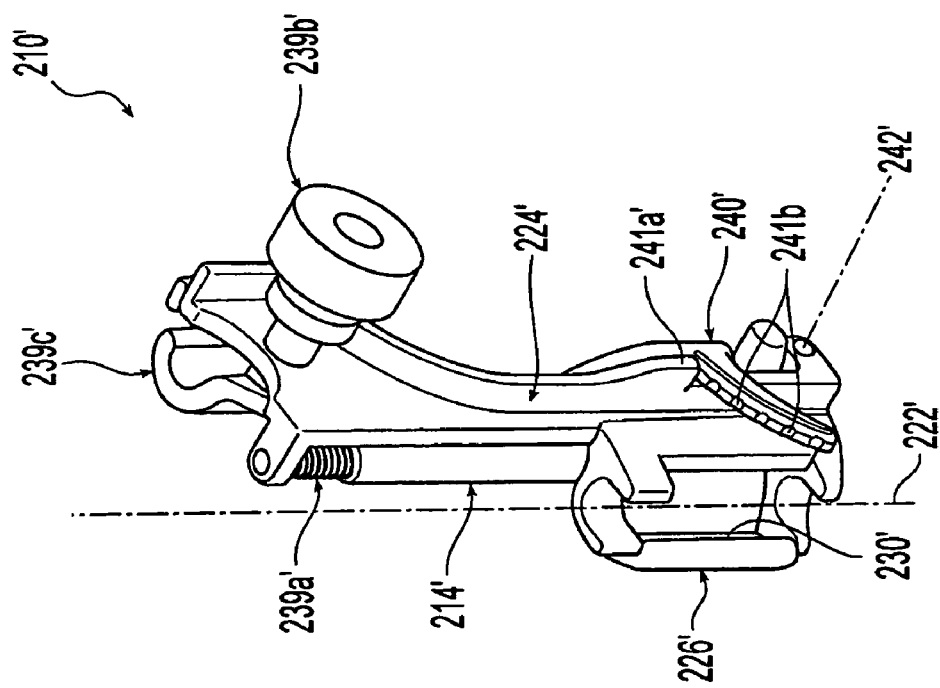
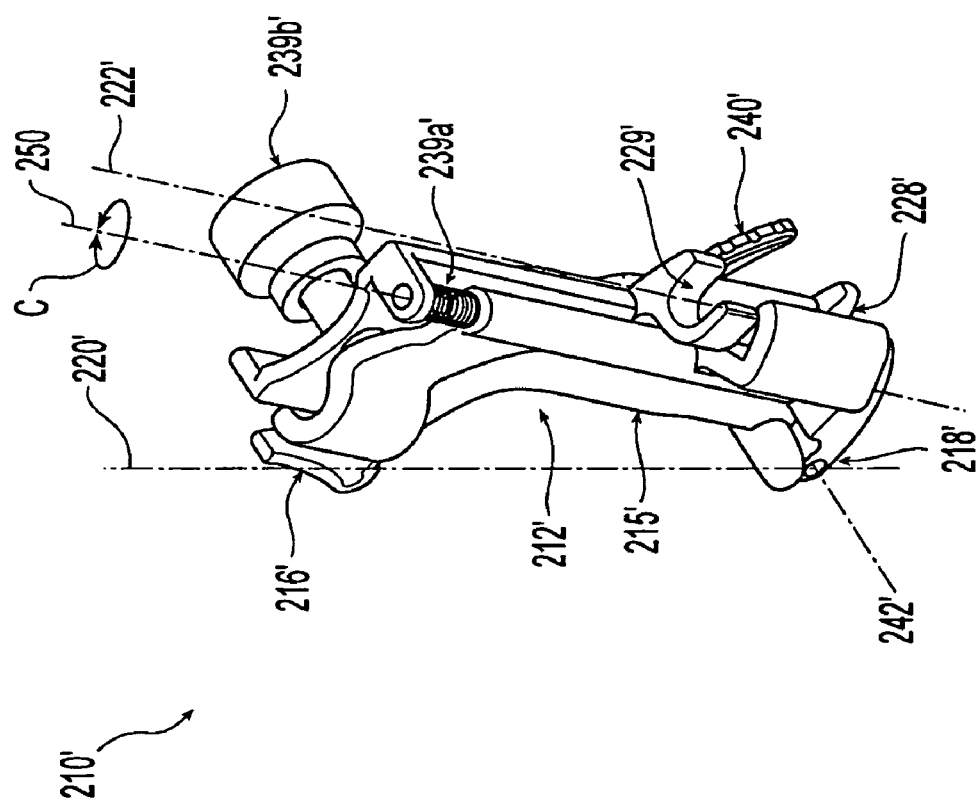

INSTRUMENT GUIDE FOR USE WITH NEEDLES AND CATHETERS

CROSS-REFERENCE TO RELATED APPLICATIONS

This application is a continuation-in-part of application Ser. No. 10/851,030 filed May 21, 2004, now abandoned, which further claims the benefit of Provisional Application No. 60/472,749 filed May 23, 2003, and the entire contents of these applications are expressly incorporated herein by reference thereto.

FIELD OF THE INVENTION

The invention relates to a guide for use with a medical imaging instrument. More particularly, the invention relates to a guide system for use in guiding elongate medical instruments into selected locations of a patient's body relative to an imaging sensor.

BACKGROUND OF THE INVENTION

Medical imaging often is conducted in tandem with the insertion of a needle, catheter, or other instrument into a subject in order to obtain a biopsy sample or perform an image-assisted medical procedure. For example, it has become increasingly accepted to perform standard radiography, fluoroscopy, ultrasound, computed tomography (CT) scanning, and magnetic resonance (MR) imaging while a medical instrument is being positioned and/or operated. In order for the imaging to be useful, it is important to provide a known alignment between the imager and medical instrument. Although it is possible to perform image-assisted medical procedures by positioning an instrument visually using an iterative process in which the instrument's trajectory is adjusted following inspection of successive images showing the instrument's position, such a technique is inefficient, slow, cumbersome and suffers from high risk associated with initial improper alignment.

For example, ultrasound is known to have use in real time needle guidance, enabling accurate targeting of internal structures during interventional procedures such as biopsy, drainage or focal therapies that can be delivered through a needle or small diameter probe. There are two fundamental techniques for ultrasound guided needle placement. One approach is known as the "freehand method," in which an ultrasound imaging transducer and needle are not coupled and thus are independently movable throughout a procedure. In this method, the needle and path to a target organ are visualized by a skilled operator who holds the transducer in one hand while advancing the needle with the other. The coordination and visual and spatial orientation skills required to simultaneously maintain the image plane in line with the needle, keep the target in view, maintain orientation to surrounding structures and manipulate the needle are substantial and demanding. Thus, the technique is not suitable for, or favored by everyone, and there is a steep and prolonged learning curve. The main advantage of the freehand method is the complete versatility allowed by total freedom of movement of both needle and ultrasound imaging transducer.

An alternate approach is known as the "needle guide method," in which a needle guide having a known orientation to the ultrasound imaging transducer is used. Such guides may be integral with the transducer, or instead may be separate, attachable accessories, and have been made as either reusable or single-use, sterile, disposable products. In the needle guide method, the guides are designed to keep any needle passing through them on a known path in the image plane, and thus avoid many of the difficulties inherent in the freehand technique. Typically, software is supplied by the ultrasound equipment manufacturer showing a virtual guide path and depth index on a real time image.

The needle guide method is less reliant on user intuition, skills and experience and has a shorter learning curve, but has several limitations that have hampered universal acceptance. First, the freehand method permits the operator to choose any size needle without restriction, whereas the needle guide method typically has required a close tolerance path for each size needle to work properly. Because of this requirement, manufacturers of prior art needle guides have devised methods that typically either require significant manipulation of the guide or multiple parts to permit a range of needle sizes to be accommodated within their guides.

Second, the freehand method permits the operator to have complete freedom of choice for entry site of the needle and angle of attack to the target, whereas the needle guide method is generally more restricting, with prior art devices typically offering only a single angle of attack in relation to the ultrasound transducer. To address this restriction, some re-usable needle guides have been designed to offer up to three different angles of attack, but such devices have required significant manual manipulation and have been considered cumbersome by some users.

Third, when using the needle guide method the needle often must be decoupled from the guide to continue some procedures, inevitably requiring additional and sometimes awkward, time consuming steps. On the other hand, the freehand method permits the operator complete freedom with the needle once it is in the desired location because the needle movement is not governed or otherwise restricted by a guide.

Fourth, the needle guide method introduces additional problems including: the requirement for a secure attachment to the transducer that does not interfere with transducer function, the possible requirement for added needle length (to allow for the length of the guide), and the issue of "dead space" that can exist between the exit of the needle tip from the guide and the entry into the skin which may contribute to misdirection of the needle. There also may be added costs to the user, although such costs may be balanced by the need for a less experienced operator and fewer complications for the patient.

To avoid some of the aforementioned disadvantages as described above, various devices are known for use in guiding medical instruments.

For example, U.S. Pat. No. 6,203,499 B1 to Imling et al. is directed to a multiple angle needle guide comprised of a body that has a slot positioned between opposing sides. The slot creates a triangular shaped gap between the opposing sides spanning a range of 45° for inclination of a needle. With this device, the angle of attack in the image plane is not fixed to a known previously determined path or paths, nor is the needle fully engaged in the guide but instead free floating in the slot. Also, the slot is not adjustable in width and therefore is only useful for a limited range of needle sizes.

U.S. Pat. No. 5,031,634 to Simon is directed to an adjustable biopsy needle-guide device that can be used to direct a variety of separate aspiration biopsy needles or tissue cutting biopsy needles to a target lesion. Sets of aligned holes are provided in a handle to aim and control the depth of the needles, with different hole sizes accommodating various needle gauges. In some applications, the required angle of insertion is guided by a goniometer or protractor, or the guide is supported by an adjustable stereotactic device attached to the patient's skin or a table top. The patent also states that if fluoroscopy is the selected imaging modality, a plastic sidearm attachment can be used to hold the handle of the device while it is being aimed or advanced into the tissues.

U.S. Pat. No. 5,052,396 to Wedel et al. is directed to a needle guide for ultrasound transducers having a means for coupling with a transducer and a multi-slotted, removable insert for receiving and guiding needles of various gauges. The configuration of the transducer, needle guide, needle, and the patient are such that a physician can firmly grasp the transducer and needle guide with one hand while maintaining contact with the patient, and manipulate the needle with the other hand.

In addition, U.S. Pat. No. 5,100,387 to Ng is directed to a disposable universal needle guide apparatus for amniocentesis. The needle guide apparatus includes a substantially horizontal base to be applied to a surface on or adjacent a zone to be punctured by a needle, an upright guide flange mounted on the base, and pivot structure associated with the flange and base. An elongated, tubular guide structure carried by the pivot structure is manually pivoted and receives the needle for guiding movement thereof at an angle determined by selective swinging of the tubular guide structure relative to the base.

Also, U.S. Pat. No. 5,941,889 to Cermak is directed to a multiple angle disposable needle guide system that includes a bracket, a mounting base, a pivoting portion of the mounting base, and a needle guide. The bracket is used to secure the needle guide system to an imaging instrument, such as an ultrasonic probe. The mounting base is secured to the imaging instrument by the bracket. The pivoting portion of the mounting base is configured to pivot along at least one axis, and the disposable needle guide is removably secured to the pivoting portion of the mounting base. The needle guide has a needle retainer member configured to retain a needle by application of a clamping force. A plurality of interchangeable needle retainer members are used so as to permit needles of various sizes to be used.

Despite these developments, there remains a need for an improved instrument guide that accommodates elongate instruments of different diameters without requiring cumbersome adjustments. There further remains a need for a guide that permits an instrument to be easily inserted and removed therefrom, particularly while the instrument (such as a needle or catheter) is in the patient. For example, it is known that with prior art instrument guides the instrument rotates or undergoes undesirable lateral movement during insertion and removal from a patient. Such lateral (sideways) movement preferably are minimized in order to avoid unnecessary patient discomfort and even trauma, while permitting axial movement into and out of the patient. Additionally, there remains a need for an instrument guide with a wide range of adjustment to accommodate different gauges of instruments.

SUMMARY OF THE INVENTION

The invention relates to a medical instrument guide including a guide body and a quick-release lever having a support portion, a gauge indicator portion, and a detent. An insert may be demountably coupled to the quick-release lever and has a plurality of notches shaped for selective engagement with said detent. The guide body and insert are configured and dimensioned to cooperate to form an instrument-receiving channel and the detent is positioned to index a plurality of different sizes of the channel. In some embodiments, the guide body and quick-release lever are pivotably coupled to each other. The guide body may have a socket and the quick-release lever may have a post, with the post being accommodated in the socket. Also, the post may demountably snap-fit in the socket.

The quick-release lever may include a pair of rails and the insert may have a pair of insert grooves, with each rail being received in one of the insert grooves. The insert may have a locking portion extending from a side thereof, wherein the locking portion may be received in a guide groove in the guide body. Further, the locking portion may releasably snap-fit in the guide groove.

The guide body may have at least one stop for limiting travel of the locking portion in the guide groove. The rails may be aligned with the guide groove when the locking portion is received in the guide groove.

In an exemplary preferred embodiment, the instrument-receiving channel may define a plurality of central instrument axes corresponding to each of the indexed sizes, and the insert may travel at an angle transverse to the central instrument axes. Also, an indicator may be visible through a slot in the insert, wherein the indicator and the detent simultaneously index the same size.

The instrument-receiving channel formed by the guide body and insert may for example accommodate elongate instruments with gauge sizes 11 through 15, or may for example accommodate elongate instruments with gauge sizes 16 through 22. Each of the gauge sizes may be indexed by engagement of the detent with a notch. Each insert may further include indicia corresponding to the indexed gauge sizes.

A lock may be demountably attached to the guide body, wherein the lock and guide body together define an unlocked position and a locked position. The lock may include a protrusion, and in the locked position the protrusion may extend into a bracket-receiving channel in the guide body. The medical instrument guide may have a lock operable between an unlocked position and a locked position, wherein in the locked position a portion of the lock extends into a channel in the guide body.

A bracket also may be provided, wherein the bracket is demountably attachable to the guide body and secured thereto when a portion of the bracket is disposed in the bracket-receiving channel and the lock is disposed in the locked position. The bracket optionally may be configured and dimensioned to support an ultrasound transducer.

In a preferred exemplary embodiment, the quick-release lever and insert may be slidably associated with each other. In some embodiments, the guide body and quick-release lever may be integrally formed. In addition, the instrument-receiving channel may have a funnel portion.

The invention also relates to a medical instrument guide including a first portion, and including a second portion having a lever, a gauge indicator, and a detent. The guide may further include a third portion demountably coupled to the second portion and having a plurality of notches shaped for selective engagement with said detent. The first and second portions may be pivotably associated with each other, the first and third portions may be configured and dimensioned to cooperate to form an instrument-receiving channel, and the detent may be positioned to index a plurality of different sizes of the channel. The instrument-receiving channel may be configured and dimensioned to accommodate a needle or a catheter. A method of guiding an elongate medical instrument into tissue may include inserting the elongate medical instrument in the instrument-receiving channel of the medical instrument guide. The second portion may be pivotable with respect to the first portion using one hand of a user. Also, the second portion may be pivotable with respect to the first portion without substantial movement of the elongate medical instrument in the instrument-receiving channel. Further, the instrument-receiving channel may define a central axis along which the elongate medical instrument is guided, and wherein the second portion may be pivotable with respect to the first portion without substantial movement of the elongate medical instrument away from the central axis. The elongate medical instrument may be a needle or a catheter. Further, the elongate medical instrument may be configured to aspirate a material, heat the tissue, cool the tissue, emit microwaves, or emit radio waves.

The invention further relates to an instrument guide kit for guiding medical instruments. The kit includes a guide body and a pair of inserts each releasably engageable with the guide body. A combination of the guide body and any one of the inserts may be configured and dimensioned to form an instrument-receiving channel, and each insert may index a plurality of discrete sizes of the instrument-receiving channel.

In addition, the invention relates to a guide for use with an imaging instrument, the guide including a first portion and a second portion proximate the first portion. A cavity may be at least partially formed by the first and second portions, the cavity having a cavity width and being configured to retain an elongate instrument therein. The cavity width may be selectively changeable to accommodate a plurality of diameters by sliding the second portion along a path with respect to the first portion. The second portion may be slidably associated with the first portion along a substantially linear path, and the cavity width may be adjustable without rotation of the second portion. The second portion may be slidable at an acute angle with respect to a central axis of the cavity, and the second portion may have an instrument-contacting surface configured to remain parallel to the central axis. Moreover, the first and second portions may be pivotable with respect to each other, and rotation of the second portion may permit generally lateral removal of an instrument from the guide without moving the instrument along the central axis. A method of guiding a elongate instrument into tissue may include inserting the elongate instrument in the cavity of the guide. The second portion may be rotatable with respect to the first portion using one hand of a user. Also, the second portion may be rotatable with respect to the first portion without substantial movement of the elongate medical instrument in the cavity. In addition, the cavity may define a central axis along which the elongate medical instrument is guided, and wherein the second portion may be rotatable with respect to the first portion without substantial movement of the elongate medical instrument away from the central axis. The medical imaging instrument may be an ultrasound transducer.

Furthermore, the invention relates to a guide for use with an imaging instrument, the guide including first and second portions each configured to engage an elongate instrument. An elongate instrument path may be defined by the first and second portions, the path having a instrument path axis. A track may define a travel axis non-parallel to the instrument path axis, the track configured to engage the second portion while permitting travel thereof along the track. Travel of the second portion along the track permits an elongate instrument diameter accommodated along the instrument path to change.

The first and second portions may be rotatably associated with each other, and rotation of the portions with respect to each other may permit generally lateral removal of the elongate instrument from the guide without moving the elongate instrument along the instrument path axis.

The second portion may index a plurality of discrete elongate instrument diameters to be accommodated along the instrument path. Also, a bracket may be provided that is configured and dimensioned for coupling to the imaging instrument, wherein the bracket is demountably associated with the first portion.

Furthermore, the invention relates to a method of guiding an elongate medical instrument into tissue comprising: forming a cavity between first and second portions coupled to each other and rotatable with respect to each other; sliding the second portion along a path with respect to the first portion to select a desired cavity dimension configured to receive and guide the elongate medical instrument therein; inserting the elongate medical instrument in the cavity. The method may further comprise at least one of: releasably locking the first and second portions to each other; releasably locking the second portion along the path to resist sliding; rotating the second portion away from the first portion so that the elongate medical instrument abuts the first portion and is free of the second portion. The first and second portions may be rotatable with respect to each other using one hand of a user. Also, the second portion may be rotated with respect to the first portion without substantial movement of the elongate medical instrument away from the first portion. The cavity may define a central axis, and wherein the second portion may be rotatable with respect to the first portion without substantial movement of the elongate medical instrument away from the central axis.

The invention additionally relates to an instrument guide including a securing portion for securing the instrument guide to an imaging transducer and an instrument engaging portion for operatively securing an instrument to the instrument guide along a guide path. At least a first portion of the instrument engaging portion may be rotatably adjustable with respect to the securing portion to allow corresponding rotational adjustment of the guide path with respect to the securing portion. The instrument may be a biopsy needle or a cryoprobe. The instrument may be configured to aspirate a material, heat or cool a tissue, emit microwaves, or emit radio waves. Also the instrument may be configured to introduce a substance to a tissue, wherein the substance may include ethanol. The instrument guide may permit capture and release in an imaging plane. The instrument guide also may include a vernier-type mechanism for exerting a user-adjustable "drag" on an instrument in the guide.

Preferred embodiments of instrument guides of the present invention may be operatively secured to an ultrasound transducer that may function in an in-plane relationship to an imaging plane. Such instrument guides also may have a single cavity for engaging multiple different needle diameters without the requirement for additional parts or attachments. A reciprocating mechanism may be provided for securely engaging, accurately guiding, and quickly releasing an instrument such as a needle, probe or catheter in an imaging plane. The angle of approach in the chosen image plane may be adjusted by an operator before or during a procedure, and may be fixed as desired. Frictional resistance of the instrument to sliding motion through the guide also may be operator-adjustable. The guides may be made of a variety of materials that may be selected for their appropriateness in disposable or reusable guides.

BRIEF DESCRIPTION OF THE DRAWINGS

Preferred features of the present invention are disclosed in the accompanying drawings, wherein:

FIG. 13 shows another top view of the guide of FIG. 1 with an insert engaged with the guide body to form an instrument-receiving channel of a second size;

FIG. 15 shows another embodiment of a medical instrument guide according to the present invention, including (15a) a first side perspective view, (15b) a second side perspective view, (15c) a third side perspective view, and (15d) a fourth side perspective view; and FIG. 16 shows yet another embodiment of a medical instrument guide according to the present invention, including (16a) a first side perspective view and (16b) a second side perspective view.

DETAILED DESCRIPTION OF THE PREFERRED EMBODIMENTS

Terms such as "upper," "lower," "front" and "back" as used herein are provided as a non-limiting examples of the orientation of features.

Figure 1:
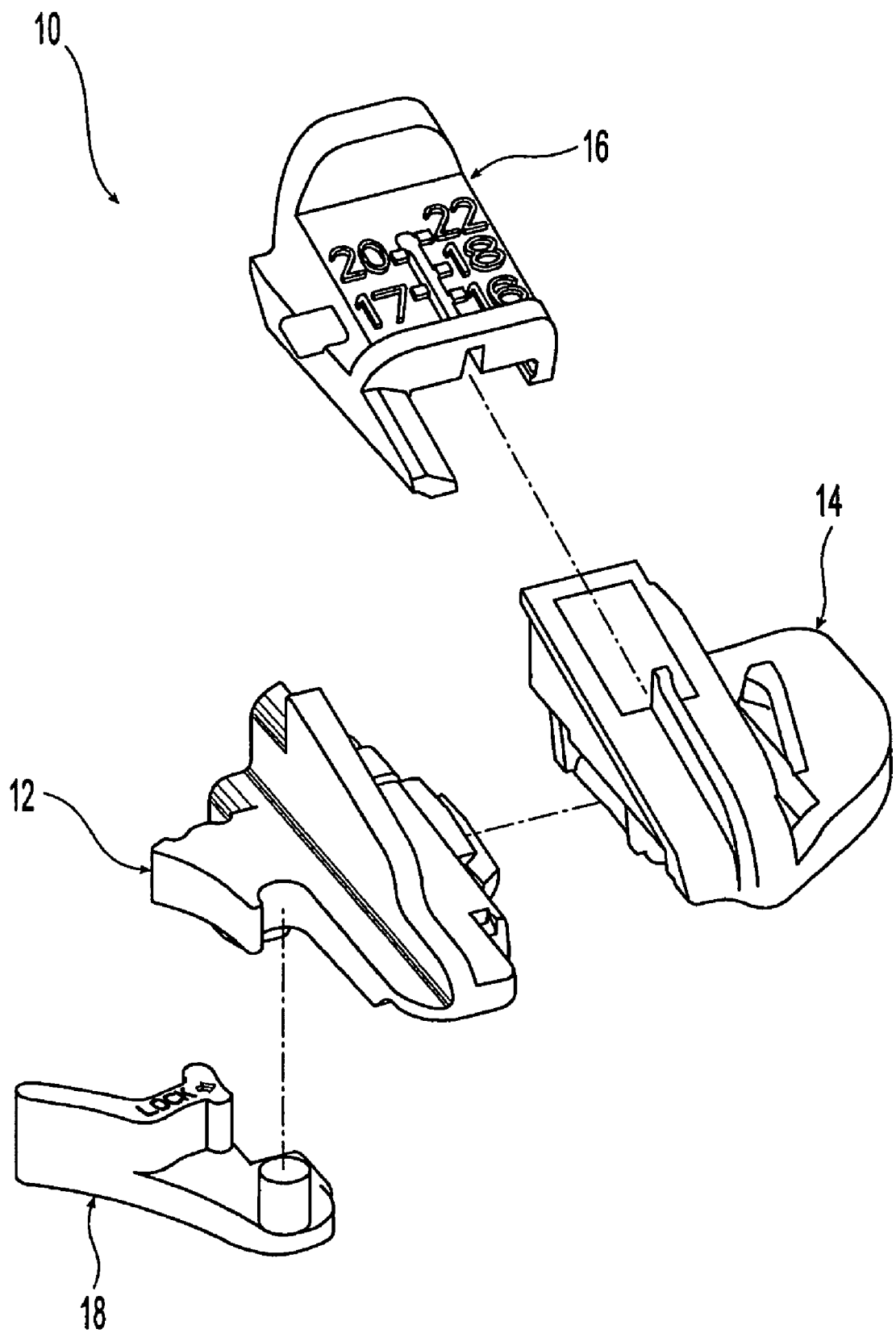
FIG. 1 shows an exploded perspective view of an embodiment of a medical instrument guide according to the present invention.
Figure 2A:
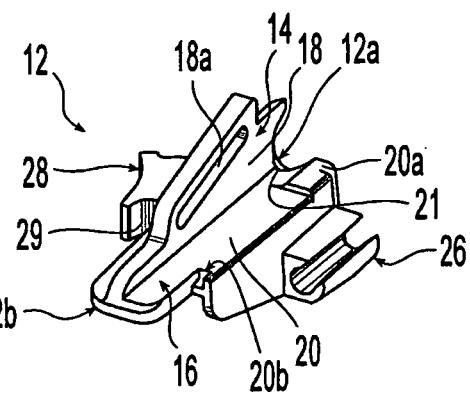
FIG. 2 shows the guide body of FIG. 1, including (2a) a side perspective view, (2b) a bottom view, (2c) a top view, (2d) a side view, (2e) another side view, (2f) a front view, and (2g) a back view.
Figure 2B:
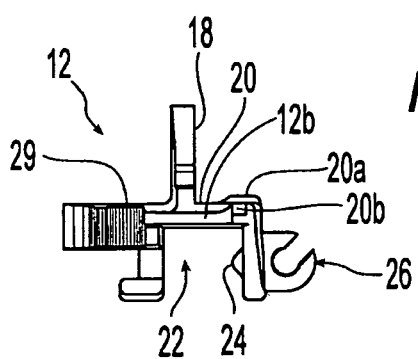
Figure 2C:
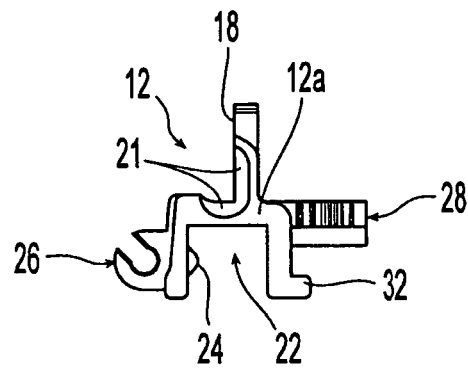
Figure 2D:
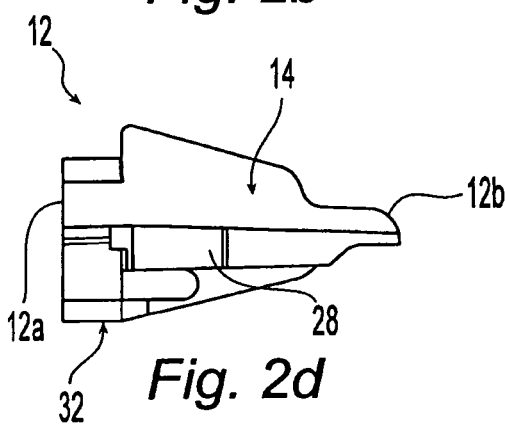
Figure 2E:
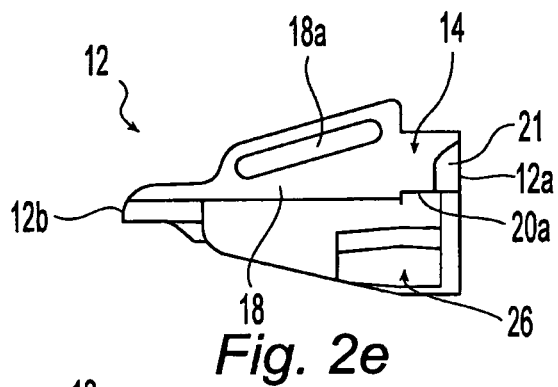
Figure 2F:
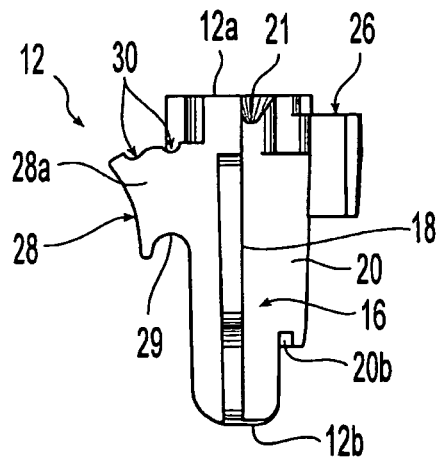
Figure 2G:
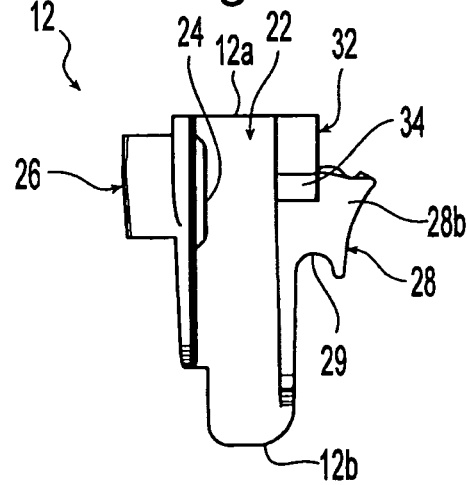
Figure 3A:
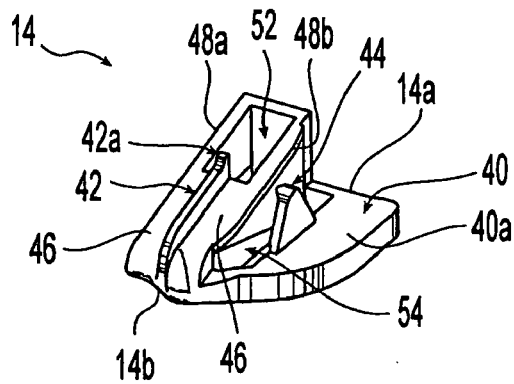
FIG. 3 shows the quick-release lever of FIG. 1, including (3a) a side perspective view, (3b) a bottom view, (3c) a top view, (3d) a side view, (3e) another side view, (3f) a front view, and (3g) a back view.
Figure 3B:
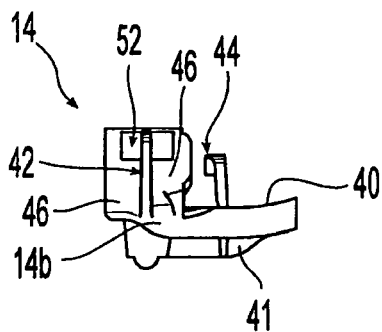
Figure 3C:
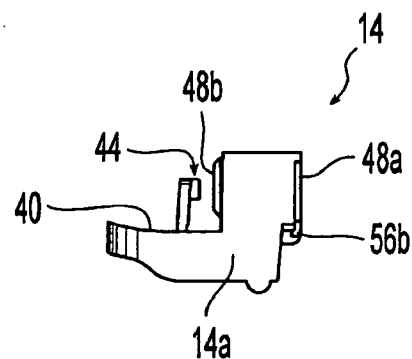
Figure 3D:
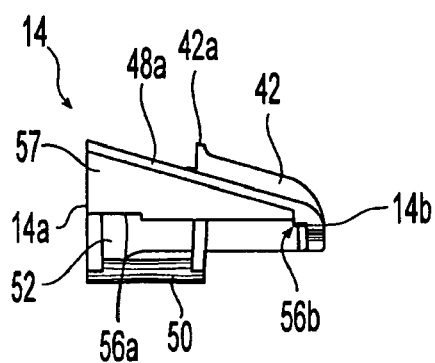
Figure 3E:
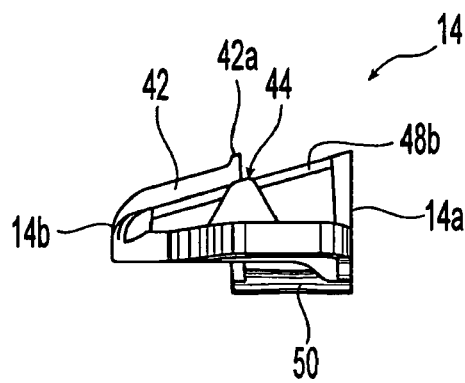
Figure 3F:
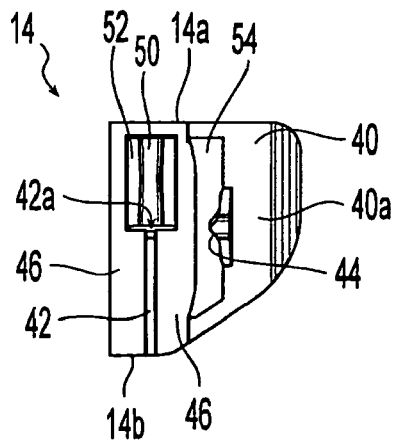
Figure 3G:
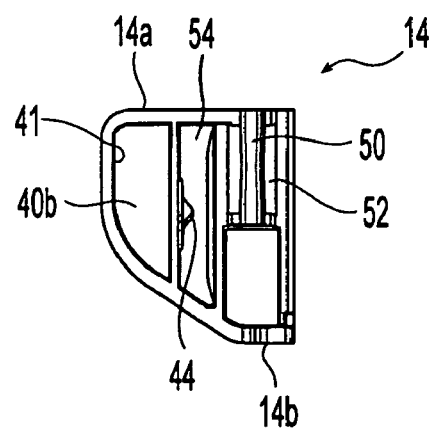
Figure 4A:
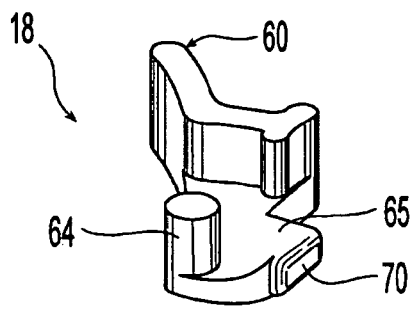
FIG. 4 shows the lock of FIG. 1, including (4a) a side perspective view, (4b) a bottom view, (4c) a top view, (4d) a side view, (4e) another side view, (4f) a front view, and (4g) a back view.
Figure 4B:
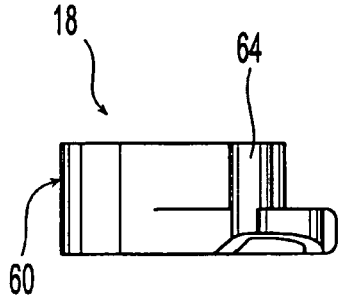
Figure 4C:
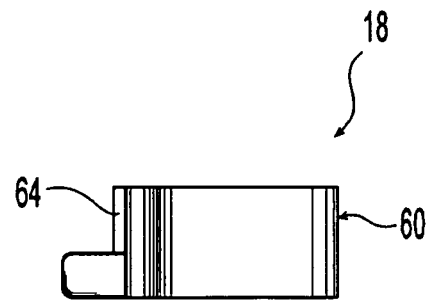
Figure 4D:
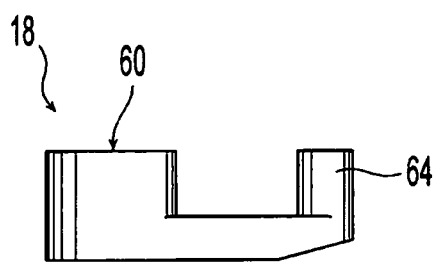
Figure 4E:
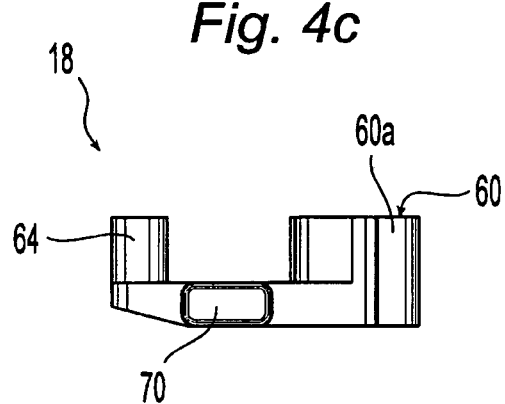
Figure 4F:
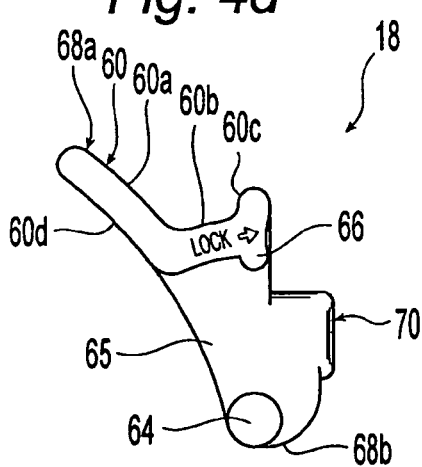
Figure 4G:
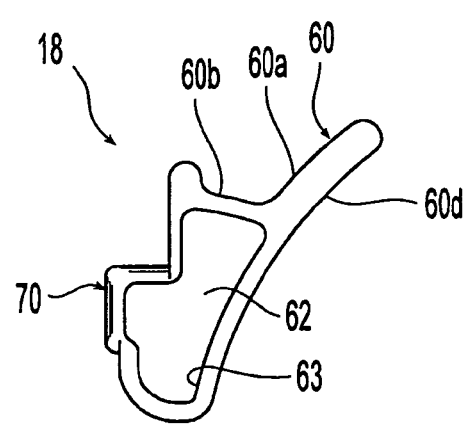
Figure 5A:
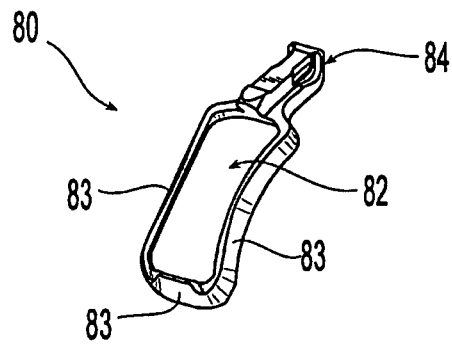
FIG. 5 shows an embodiment of a bracket according to the present invention for demountable attachment to the guide body of FIG. 1, including (5a) a side perspective view, (5b) a bottom view, (5c) a top view, (5d) a side view, (5e) another side view, (5f) a front view, and (5g) a back view.
Figure 5B:
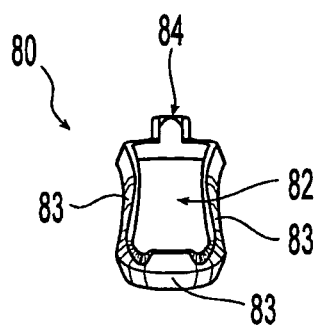
Figure 5C:
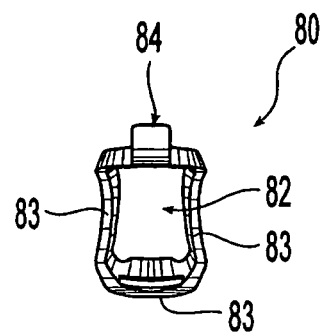
Figure 5D:
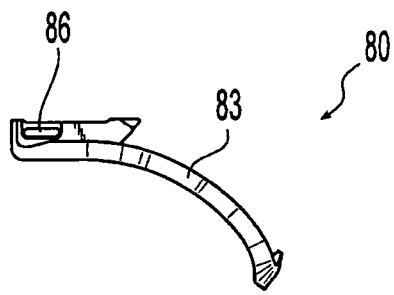
Figure 5E:
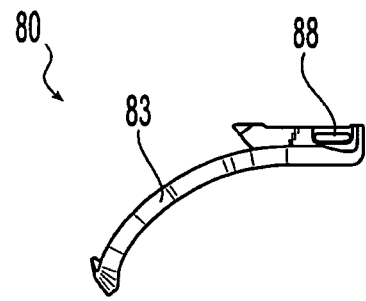
Figure 5F:
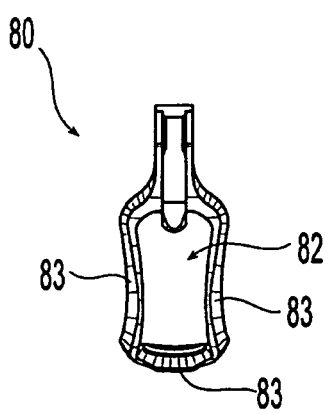
Figure 5G:
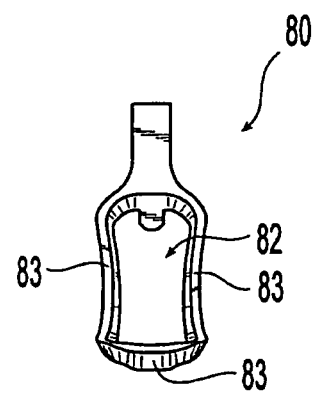

Referring initially to FIG. 1, a medical instrument guide according to one exemplary embodiment of the present invention is shown. Medical instrument guide 10 includes a guide body 12, a quick-release lever 14, an insert 16, and a lock 18.

As will be described in detail below, guide body 12 and insert 16 are configured and dimensioned to cooperate to form an instrument-receiving channel.

Turning to FIG. 2, guide body 12 includes supports 14, 16 defining respective support surfaces 18, 20 upon which an elongate medical instrument such as a needle will abut. In the preferred exemplary embodiment, support surfaces 18, 20 are disposed at about 90° with respect to each other. In alternate embodiments, these surfaces may be at a different angle so long as they are disposed transverse to one another. Guide body 12 preferably has an upper end 12a and a lower end 12b. Proximate upper end 12a, an inwardly curvate, tapering lip 21 may bridge support surfaces 18, 20 for use in guiding a member along these surfaces. A guide groove 18a extends in support surface 18 transverse to support surface 20. In addition, a shoulder 20a protrudes proximate upper end 12a of support surface 20, while a recess or notch 20b is disposed proximate lower end 12b of support surface 20.

A securing region 22 is provided for attaching guide 10 for example to an imaging instrument, as will be described shortly. In one preferred exemplary embodiment as shown in FIG. 2, securing region 22 is configured and dimensioned as a channel. Also, a first protrusion 24 is provided within securing region 22 for permitting a releasable mechanical interlock with an object inserted in securing region 22. For example, if a portion of a bracket for supporting an imaging instrument is inserted in securing region 22, protrusion 24 may be received in a like-shaped groove therein.

The preferred exemplary embodiment of guide body 12 includes a coupling region 26 that may be configured as a generally cylindrical channel or socket for providing a pivotable connection with a suitably shaped member. Preferably coupling region 26 is disposed closer upper end 12a than lower end 12b. In the preferred embodiment, coupling region 26 is disposed proximate upper end 12a.

Guide body 12 further includes a lock indexing section 28 with arcuate guide surface 29 and indexing positions 30. In one preferred exemplary embodiment, section 28 includes a front surfaces 28a that provides sufficient surface area for accommodating a portion of a user's finger such as the fleshy tip of a user's thumb or index finger. Lock indexing section 28 is provided to be operably associated with lock 18. A shoulder 32 is provided on a back side of guide body 12, and a cutout 34 is included for accommodating a portion of lock 18, as will be described.

Referring next to FIG. 3, quick-release lever 14 is shown including a support portion 40, a gauge-indicator portion 42, and a detent 44. Quick-release lever 14 preferably has an upper end 14a and a lower end 14b. Similar to guide body 12, one preferred exemplary embodiment of support portion 40 includes a front surface 40a that provides sufficient surface area for accommodating a portion of a user's finger such as the fleshy tip of a user's thumb or index finger. A back surface 40b with raised wall 41 provides further sufficient surface area for accommodating a portion of a user's other finger such as the fleshy tip of a user's thumb or index finger. Thus, support portion 40 may be grasped between two fingers each resting on a surface 40a, 40b, with raised wall 41 providing additional leverage.

In addition, gauge-indicator portion 42 protrudes from a support surface 46 and preferably is generally disposed about halfway across a width thereof. Portion 42 preferably is disposed closer lower end 14b than upper end 14a. In the preferred exemplary embodiment, portion 42 extends from about midway between upper and lower ends 14a, 14b, respectively, to proximate lower end 14b. A nub 42a extends outward from an end of gauge-indicator portion 42.

Rails 48a, 48b preferably are positioned on opposing sides of support surface 46 for receiving insert 16, as will be described. A pivot member 50 preferably is provided proximate upper end 14a, and in the preferred exemplary embodiment is generally cylindrical and is configured and dimensioned for demountable snap-fitting and pivoting in socket 26.

Detent 44 preferably extends toward gauge-indicator portion 42 and is aligned with nub 42a thereof. In a preferred exemplary embodiment, detent 44 has a generally triangular tip as shown for example in FIGS. 3f and 3g.

Windows 52, 54 optionally may be provided in gauge-indicator portion 42. The cut-out 52 permits inspection of pivot member 50, particularly when pivotably associated with socket 26 of guide body 12, and also permits socket 26 to articulate therein. Cut-out 54 permits visualization behind gauge-indicator portion 42 and concomitantly provides a contrasting field of view when inspecting detent 44.

A recess or ledge 56a also is provided proximate upper end 14a along a side surface 57 of gauge-indicator portion 42. Ledge 56a is configured and dimensioned to receive shoulder 20a of guide body 12 when pivot member 50 is pivotably associated with socket 26. Additionally, a shoulder 56b is provided proximate lower end 14b along side surface 57, and is configured and dimensioned to be received in notch 20b of guide body 12 when pivot member 50 is pivotably associated with socket 26. In an alternate embodiment, however, each of guide body 12 and gauge-indicator portion 42 may be provided with one or more shoulders or one or more mating recesses for facilitating coupling and alignment of guide body 12 with respect to gauge-indicator portion 42.

Turning now to FIG. 4, lock 18 will be described. A lever 60 is provided for demountable and pivotable attachment to guide body 12 and which is operable between unlocked and locked, indexed positions thereon. Lever 60 includes side surfaces 60a, 60b, 60c adjacent but transversely oriented each other, as well as opposed side surface 60d. Side surfaces, 60a, 60b, 60c together and side surface 60d provide sufficient surface area for accommodating a portion of a user's finger such as the fleshy tip of a user's thumb or index finger. Thus, lock lever 60 may be grasped between two fingers each resting on either surfaces 60a, 60b or on surface 60c. Lock 18 further includes a back surface 62 with raised wall 63 that provides further sufficient surface area for accommodating a portion of a user's other finger such as the fleshy tip of a user's thumb or index finger. When lock 18 is demountably coupled to guide body 12, the assembled lock 18 and guide body 12 may be grasped between two fingers each resting on a surface 62, 28a, respectively, with raised wall 63 providing additional leverage.

A post 64 extends from a front surface 65 of lock 18, preferably generally perpendicular thereto. Post 64 is provided for pivoting in arcuate guide surface 29 of guide body 12. Lock 18 is configured and dimensioned such that when post 64 abuts arcuate guide surface 29, finger 66 of lock 18 indexes with lock indexing section 28 of guide body 12. In a preferred exemplary embodiment, lever 60 is provided at an upper end 68a of lock 18, while post 64 is provided at a lower end 68b.

A second protrusion 70 extends from a side of lock 18, and is positioned, configured and dimensioned such that when post 64 is seated against arcuate guide surface 29 and finger 66 indexes with lock indexing section 28 of guide body 12, protrusion 70 may be selectively disposed to oppose first protrusion 24 of guide body 12 and extend within securing region 22. In combination, first and second protrusions 24, 70 thus permit a releasable mechanical interlock with an object inserted in securing region 22, as previously discussed. Second protrusion may be disposed in a retracted position within cutout 34 of shoulder 32 of guide body 12 corresponding to the unlocked indexed position of lock 18, or may be disposed in an extended position beyond cutout 34 of shoulder 32 and within securing region 22 corresponding to the locked indexed position of lock 18. Thus, for example, if a portion of a bracket for supporting an imaging instrument is inserted in securing region 22, protrusions 24, 70 may be received in like-shaped grooves therein.

A preferred exemplar bracket 80 for supporting an imaging instrument and for coupling to guide 10 is shown in FIG. 5. Bracket 80 includes an imaging instrument receiving opening 82 framed by support walls 83, and a coupling section 84 for connecting to guide 10. Grooves 86, 88 are disposed on opposing sides of coupling section 84, so that when bracket 80 is connected to guide 10, protrusions 24, 70 of guide body 12 and lock 18, respectively, may be received in and mate with like-shaped grooves 86, 88 to releasably secure coupling section 84 to guide 10. As can be seen for example in FIGS. 5d and 5e, support walls 83 are curvate. Preferably, bracket 80 is configured and dimensioned such that when guide 10 is coupled thereto and an imaging instrument is disposed in receiving opening 82, an instrument received in the instrument-receiving channel of guide 10 is aligned or readily alignable with the imaging instrument.

Turning to FIGS. 6 and 7, first and second inserts 16, 110 according to the present invention are shown. In the preferred exemplary embodiment, each insert is configured for selecting an instrument-receiving channel sized to accommodate each of five different gauge sizes. In alternate embodiments, however, each insert may be sized to accommodate any number of different gauge sizes, from a single gauge size to a plurality of gauge sizes. Exemplary insert 16 is configured for use with gauge sizes 16, 17, 18, 20 and 22, while exemplary insert 110 is configured for use with gauge sizes 11, 12, 13, 14 and 15. However, other gauge sizes may be provided to suit a particular need.

Because guide 10 may be used, for example, with needles and catheters, the sizes of these devices are correlated in Tables 1 and 2 for reference. Needles are typically measured by Birmingham or Stubs' gauge, so that the larger the gauge number, the smaller the needle outside diameter. Catheters are measured in French (Fr.) size, so that 3 Fr. is equal to 1 millimeter in outside diameter. Thus, even though inserts 16, 110 are provided with indicia 90, 112 indicating gauge size, other indicia may be provided instead or in addition to indicate dimensions in millimeters, inches, or French size.

TABLE 1

| Gauge No. | Outer Dia. (in.) | Outer Dia. (mm) |
| --- | --- | --- |
| 10 | 0.134 | 3.40 |
| 11 | 0.120 | 3.05 |
| 12 | 0.109 | 2.77 |
| 13 | 0.095 | 2.41 |
| 14 | 0.083 | 2.11 |
| 15 | 0.072 | 1.83 |
| 16 | 0.065 | 1.65 |
| 17 | 0.058 | 1.47 |
| 18 | 0.049 | 1.24 |
| 19 | 0.042 | 1.07 |
| 20 | 0.035 | 0.89 |
| 21 | 0.032 | 0.81 |
| 22 | 0.028 | 0.71 |
| 23 | 0.025 | 0.64 |
| 24 | 0.022 | 0.56 |
| 25 | 0.020 | 0.51 |

TABLE 2

| Size (Fr.) | Outer Dia. (in.) | Outer Dia. (mm) |
|---|---|---|
| 3 | 0.039 | 1.00 |
| 4 | 0.053 | 1.33 |
| 5 | 0.066 | 1.67 |
| 6 | 0.079 | 2.00 |
| 7 | 0.092 | 2.33 |
| 8 | 0.105 | 2.67 |
| 9 | 0.118 | 3.00 |
| 10 | 0.131 | 3.33 |
| 11 | 0.144 | 3.67 |
| 12 | 0.158 | 4.00 |
| 13 | 0.170 | 4.33 |
| 14 | 0.184 | 4.67 |
| 15 | 0.197 | 5.00 |
| 16 | 0.210 | 5.33 |
| 17 | 0.223 | 5.67 |
| 18 | 0.236 | 6.00 |

First and second inserts 16, 110 are similar in design, and thus only first insert 16 will be described in detail herein. However, the features described for insert 16 are likewise descriptive of the design of insert 110. Insert 16 preferably has an upper end 92 and a lower end 94. Proximate ends 92, 94 are disposed respective supports 96, 98 that each provide sufficient surface area 100, 102 for accommodating a portion of a user's finger such as the fleshy tip of a user's thumb or index finger. Thus, insert 16 may be grasped between two fingers each resting on a surface 100, 102, for positioning of insert 16 on quick-release lever 14 and for selective movement of insert 16 thereon.

Insert 16 is provided with a plurality of notches 104 shaped for selective engagement with detent 44 of quick-release lever 14, thus providing a plurality of discrete stops. Each notch 104 corresponds to one of the gauge sizes also indicated by indicia 90. Additional indicia 106, as for example shown in FIG. 6*f*, correspond to each notch 104 and a particular gauge size. A central slot 108 is configured and dimensioned for receiving gauge-indicator portion 42 of quick-release lever 14 and nub 42*a* thereof when insert 16 is coupled to quick-release lever 14. End 108*a* of slot 108 serves as a stop for limiting travel of insert 16 when nub 42*a* of gauge-indicator portion 42 of quick-release lever 14 abuts end 108*a*.

Figure 6A:
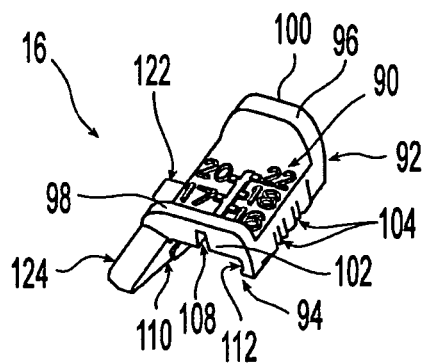
FIG. 6 shows a first embodiment of an insert according to the present invention, including (6a) a side perspective view, (6b) a bottom view, (6c) a top view, (6d) a side view, (6e) another side view, (6f) a front view, and (6g) a back view.
Figure 6B:
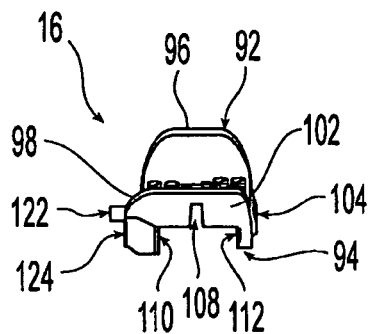
Figure 6C:
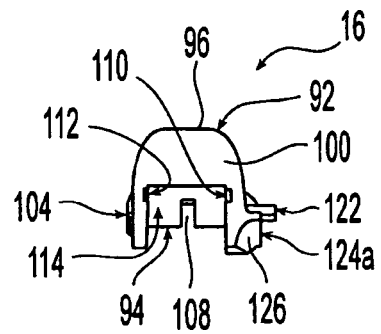
Figure 6D:
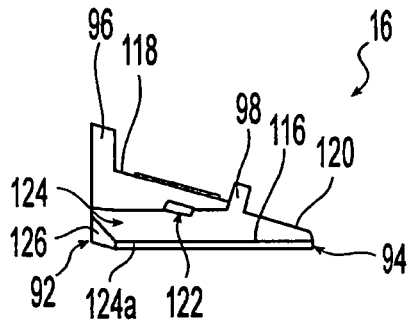
Figure 6E:
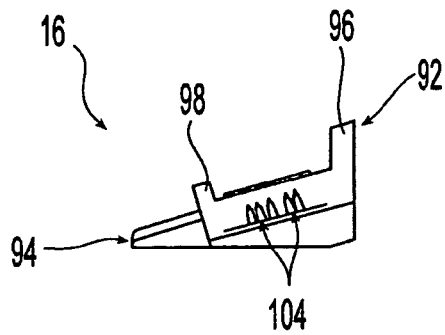
Figure 6F:
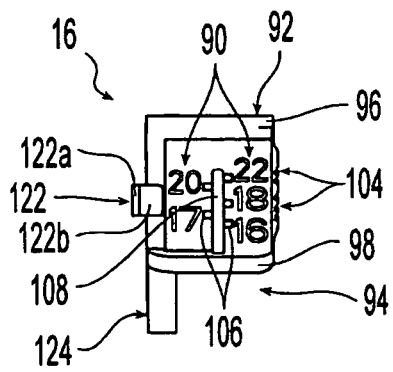
Figure 6G:
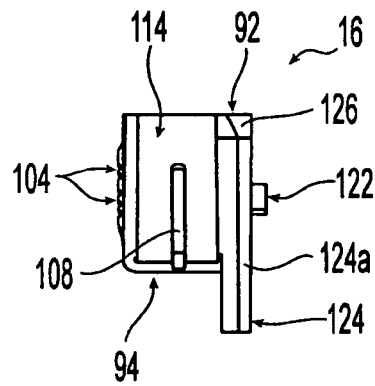
Figure 7A:
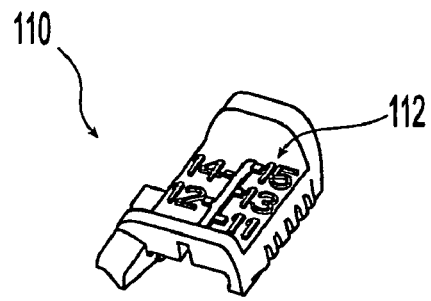
FIG. 7 shows a second embodiment of an insert according to the present invention, including (7a) a side perspective view, (7b) a bottom view, (7c) a top view, (7d) a side view, (7e) another side view, (7f) a front view, and (7g) a back view.
Figure 7B:
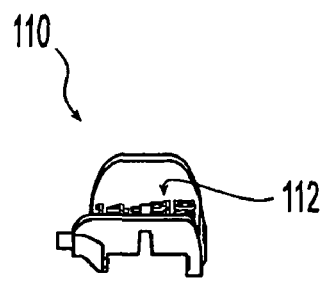
Figure 7C:
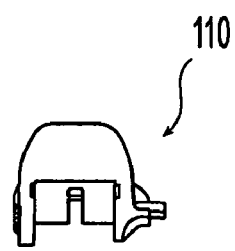
Figure 7D:
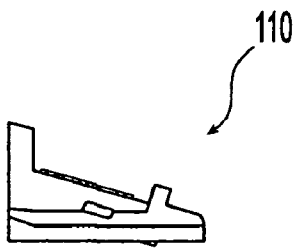
Figure 7E:
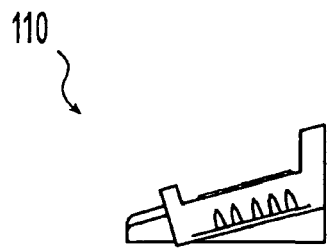
Figure 7F:
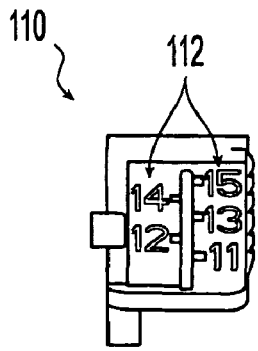
Figure 7G:
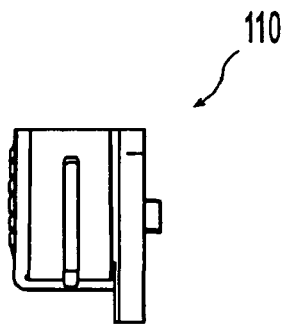

Grooves 110, 112 are provided on a back side 114 of insert 16 for operable association with rails 48*a*, 48*b* of quick-release lever 14. Thus, rails 48*a*, 48*b* ride along grooves 110, 112 to guide the movement of insert 16. Preferably, grooves 110, 112 are parallel, and rails 48*a*, 48*b* also are parallel so that they all may be aligned with respect to each other for movement. FIG. 6*d* shows a first side of insert 16 having a generally triangular profile. Grooves 110, 112 preferably are disposed generally transverse to lower edge 116 but generally parallel to upper edges 118 and/or 120.

In addition, insert 16 includes a locking portion 122 for releasable engagement with guide groove 18*a* in guide body 12. Locking portion 122 is disposed about halfway between upper and lower ends 92, 94 on a side opposite of guide body 10 opposite notches 104. In some embodiments, locking portion 122 may include a raised portion 122*a* and a lower portion 122*b* to facilitate engagement with guide groove 18*a*.

An elongate support 124 with a support surface 124*a* is provided for use in guiding a member therealong, and serves this purpose preferably in combination with support surfaces 18, 20 of guide body 12. In the exemplary preferred embodiment, support 124 extends the entire length of insert 16 and is disposed on the same side as locking portion 122. Proximate upper end 92, an inwardly curvate, tapering lip 126 is disposed for use in guiding a member along support surface 124*a*. The combination of tapering lip 126 with tapering lip 21 bridging support surfaces 18, 20 of guide body 12 creates a funnel-style insertion point that for example, facilitates quick instrument placement in darkened ultrasound suites.

Figure 8A:
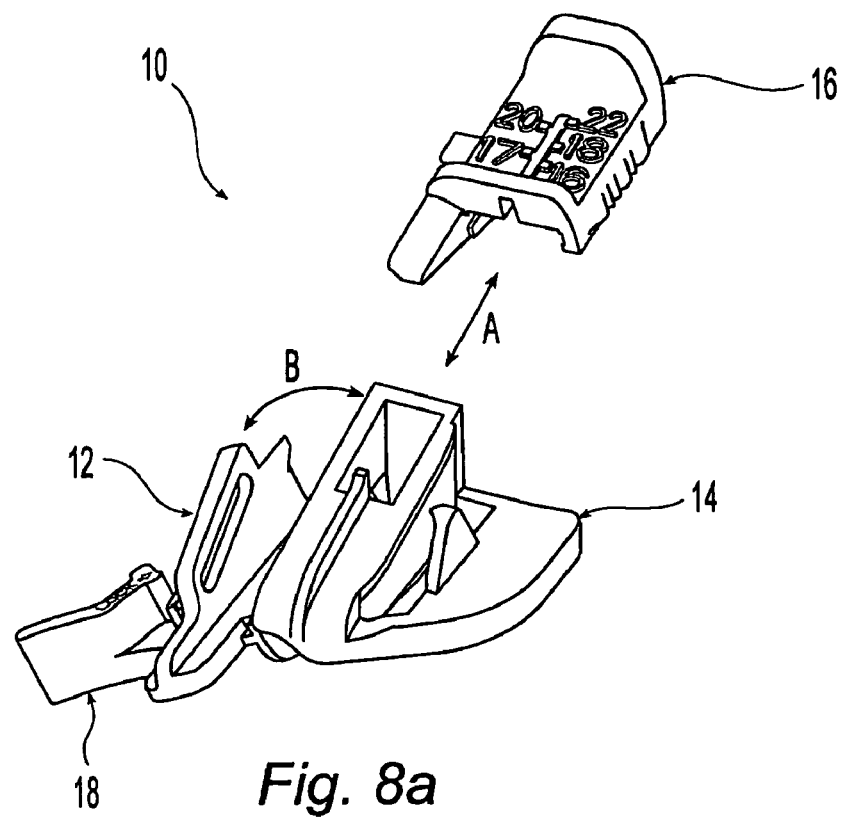
FIGS. 8a and 8b show perspective views of the guide of FIG. 1 with an insert being coupled thereto.
Figure 8B:
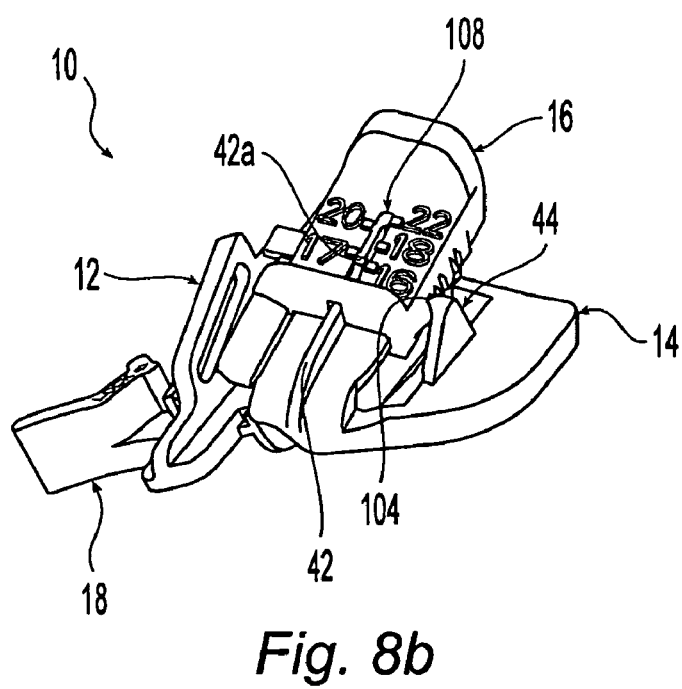

With each of the components of guide 10 now described, next the operation of guide 10 is explained. A user may select an appropriate insert 16, 110 according to the size instrument to be used with guide 10. For example, if a user desires to guide an 18 gauge needle using guide 10, then insert 16 is appropriate, whereas for a 12 gauge needle insert 110 may be used. As shown in FIG. 8, guide 10 is disposed in an open position. Insert 16 may be installed on quick-release lever 14 by moving insert 16 in the direction of arrow A, as shown in FIG. 8*a*, so that grooves 110, 112 slide along rails 48*a*, 48*b* of quick-release lever 14, as previously described. Preferably, insert 16 may only be demountably attached to quick-release lever 14 when guide 10 is disposed in the open position with guide body 12 pivoted away from quick-release lever 14, as shown with arrow B. As shown in FIG. 8*b*, when insert 16 is coupled to quick-release lever 14, detent 44 may be indexed to a notch 104 to select the desired gauge, in a ratchet-like relationship. Also, gauge-indicator portion 42 and nub 42*a* of quick-release lever 14 are disposed coaxially with central slot 108 and received therein.

Figure 9A:
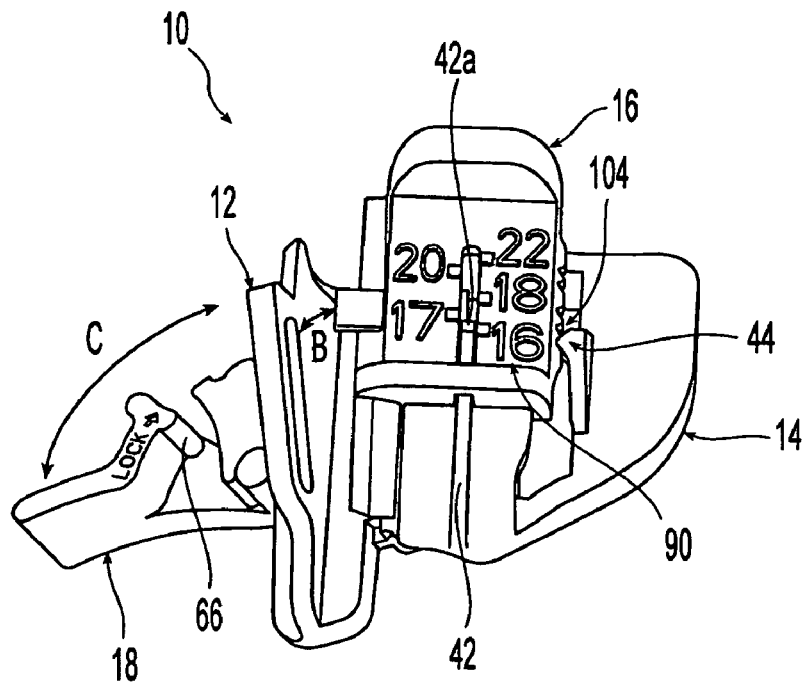
FIGS. 9a and 9b show perspective views of the insert of FIG. 8 being positioned at different index positions corresponding to different gauges accommodated by the instrument-receiving channel of the guide of FIG. 1.
Figure 9B:
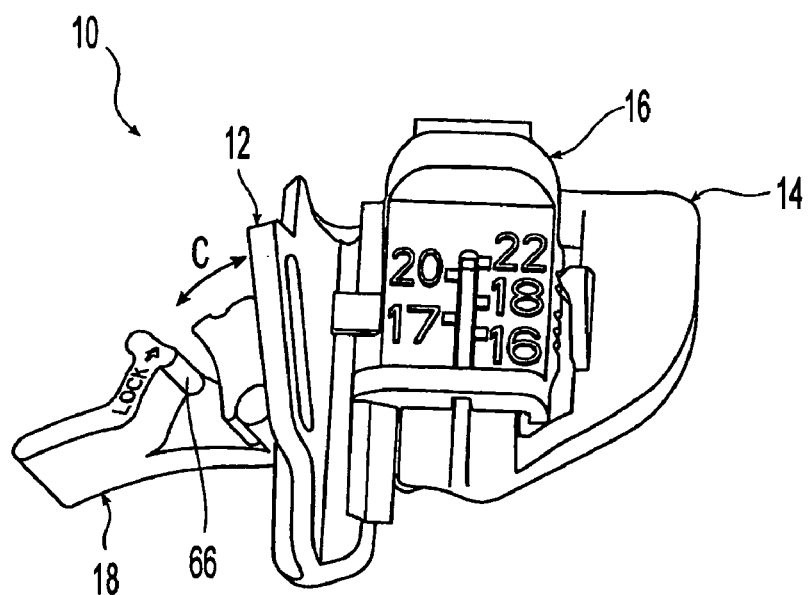

As can be seen in FIG. 9, when a particular gauge is selected, detent 44 indexes with a notch 104 corresponding to numerical and associated indicia 90, 106, with nub 42*a* generally aligned with indicia 90, 106. Thus, a user has several indicators that confirm the selection of a particular gauge size. Also shown in FIG. 9, lock 18 is shown disengaged entirely from arcuate guide surface 29 of lock indexing section 28, for clarification purposes only. In use, finger 66 of lock 18 would be engaged with lock indexing section 28 of guide body 12, and would be moveable in the direction of arrow C as shown. To demonstrate the selection of an alternate gauge size permitted by insert 16, FIG. 9*b* shows the positioning of insert 16 on quick-release lever 14 so that 22 gauge is selected.

Figure 10:
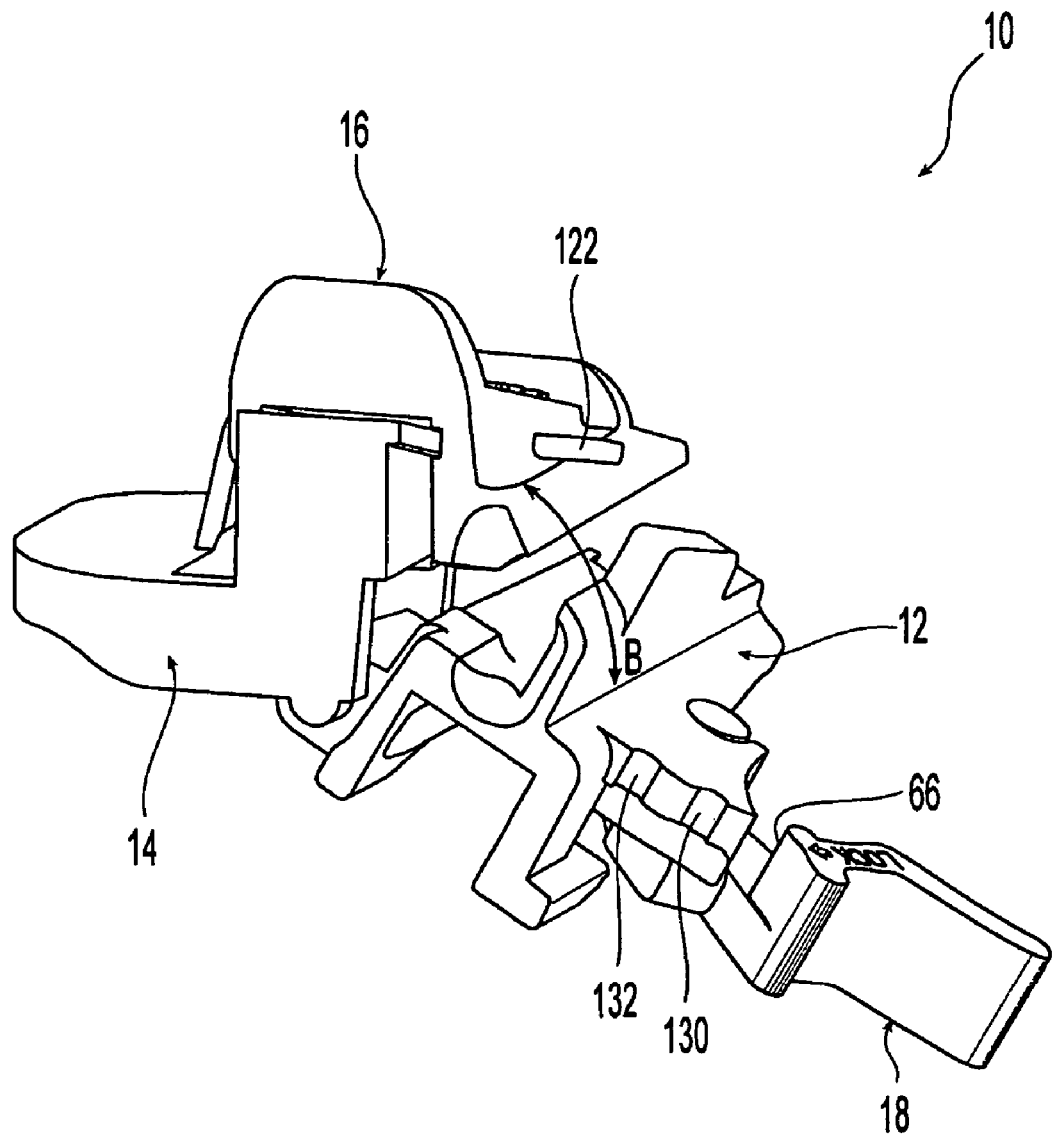
FIG. 10 shows a top perspective view of the guide of FIG. 1 with an insert disengaged from the guide body.

Another perspective view of guide 10 is shown in FIG. 10. As can be seen, finger 66 of lock 18 may be engaged with lock indexing section 28 of guide body 12 in a first recess 130 corresponding to an unlocked position of lock 18, or in a second recess 132 corresponding to a locked position of lock 18 as previously described.

Guide body 12 and quick-release lever 14 are rotatably associated with each other and may be pivoted in the direction of arrow B. When rotated so that locking portion 122 of insert 16 engages guide groove 18*a* of guide body 12, the instrument-receiving channel of guide 10 is formed.

Figure 11:
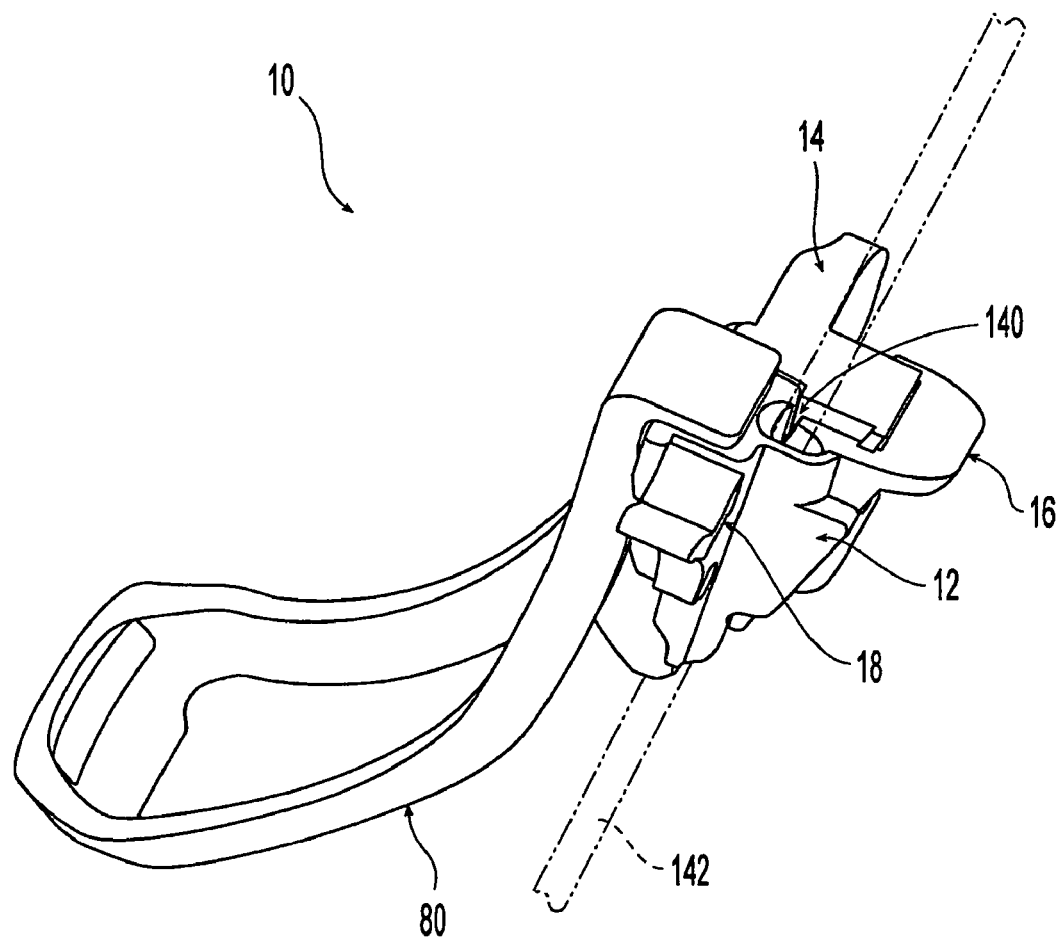
FIG. 11 shows a side perspective view of the guide of FIG. 1 with a bracket coupled thereto and an insert engaged with the guide body.

Yet another perspective view of guide 10 is shown in FIG. 11, with an instrument-receiving channel 140 formed for receiving an instrument 142 (shown in phantom) therein. Bracket 80 is shown demountably attached to guide body 12.

Figure 12:
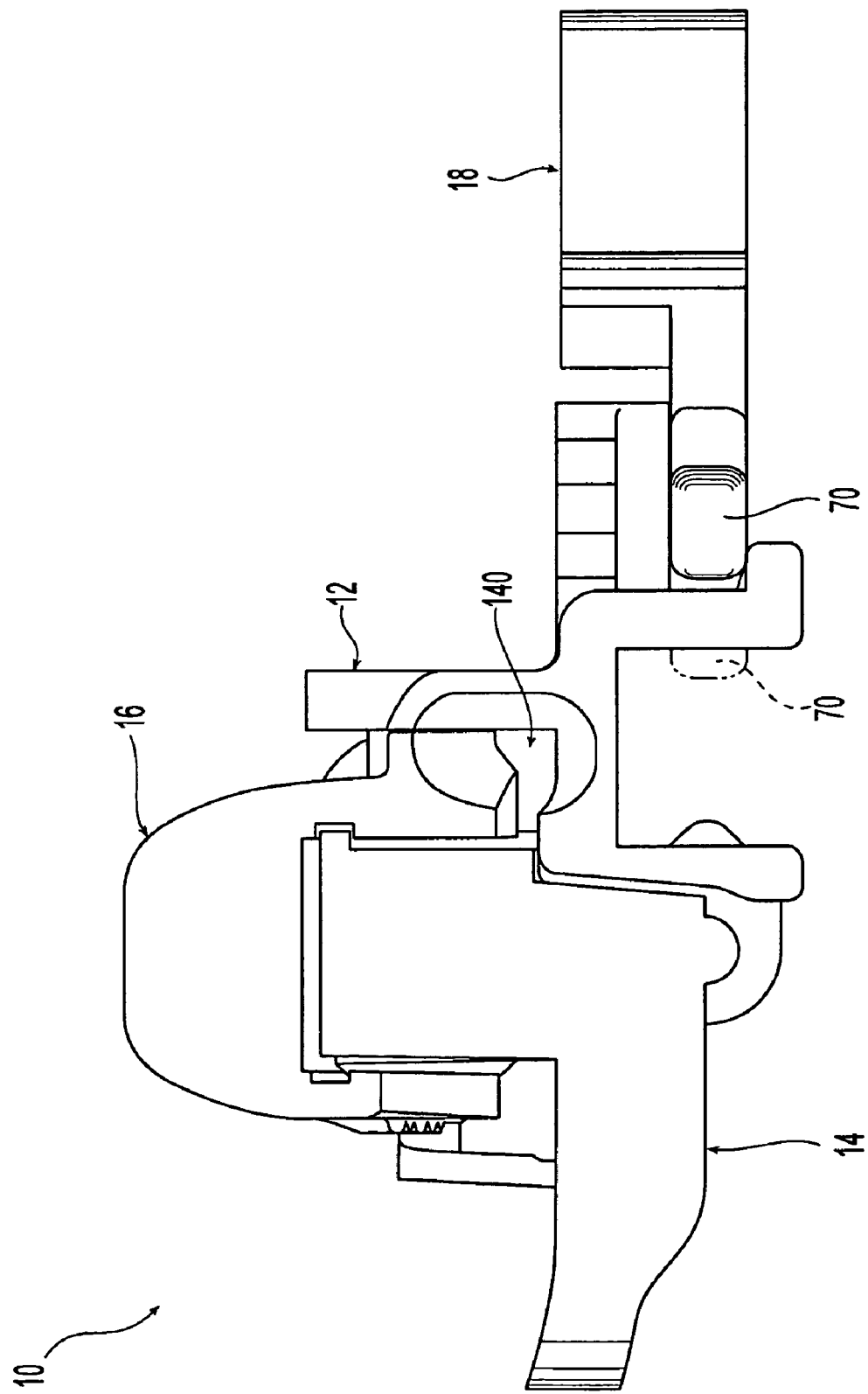
FIG. 12 shows a top view of the guide of FIG. 1 with an insert engaged with the guide body to form an instrument-receiving channel of a first size.

Turning to FIGS. 12 and 13, two views of guide 10 are shown with insert 16 disposed in different positions thus selecting different gauge sizes. As can be seen in FIG. 12, instrument-receiving channel 140 has a first size, while in FIG. 13 the instrument-receiving channel 140 has a second size smaller than the first size. This suggests that guide 10 is set in FIG. 12 to accommodate a smaller gauge (and hence larger outer diameter) instrument than in FIG. 13. Also, second protrusion 70 of lock 18 is shown in the completely disengaged position, as well as shown in phantom where indicating where it would be disposed when finger 66 of lock 18 is disposed in second recess 132 of lock indexing section 28 of guide body 12, corresponding to a locked position of lock 18

Figure 14A:
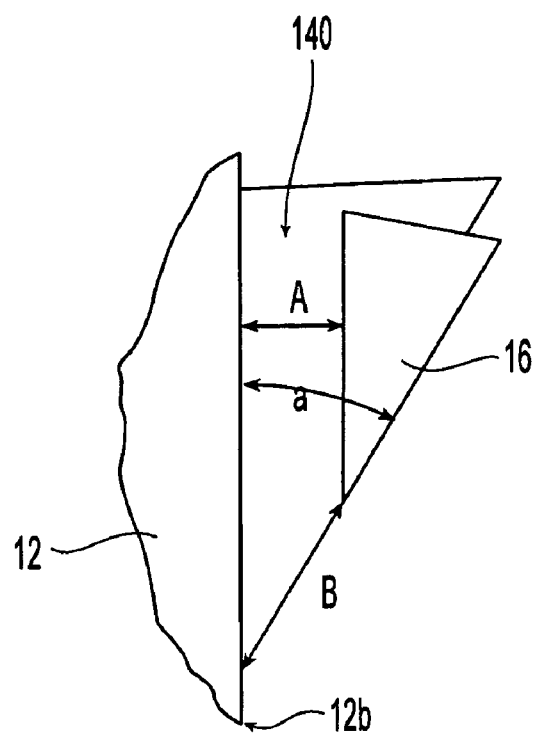
FIGS. 14a and 14b schematically demonstrate the operation principle behind a preferred exemplary embodiment of the selectable size instrument-receiving channel.
Figure 14B:
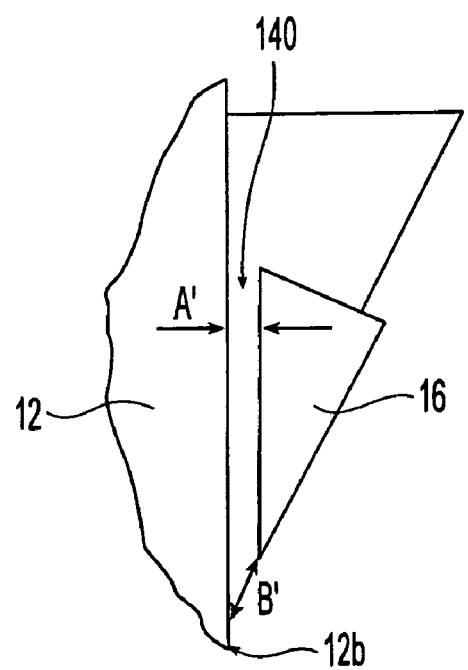

The operation principle behind a preferred exemplary embodiment of the selectable size instrument-receiving channel 140 is clarified in FIGS. 14*a* and 14*b*, which show a simplified representation of the mechanism used to change the size of this path. In these simplified drawings, two sizes of instrument-receiving channel 140 are shown as distances A and A', respectively, while two distances of insert 16 along rails 48*a*, 48*b* of quick-release lever 14 are shown as B and B', respectively. As evident from the figures, when insert 16 travels toward lower end 12*b* of guide body 12, A'<A and B'<B thereby creating a more narrow instrument-receiving channel 140. In the preferred exemplary embodiment, insert 16 travels along rails 48*a*, 48*b* at an angle α that is about 45 degrees or less. Therefore, the distance moved along the inserts path corresponds to a shorter distance change in the "diameter" or size of the needle path. In this manner, relatively fine adjustments in the needle path diameter can be made. Also, in the preferred exemplary embodiment, a plurality of central axes are definable in instrument-receiving channel 140 due to the movable insert, preferably with each of the central axes being parallel to one another.

As disclosed herein, the bracket 80 and guide 10 may provide users such as physicians with a tool for performing needle-guided or catheter procedures with the use of ultrasound transducers. As known in the art, during use, a transducer may first be disposed in a transducer cover. The cover preferably is installed with an appropriate amount of gel or other lubricating agent inside the cover and/or on the transducer face. The cover is pulled tightly over the transducer face to remove wrinkles and air bubbles, taking care to avoid puncturing the cover. The cover may be secured to the transducer with elastic bands or other means. An appropriate insert 16 is selected based on the gauge size required, and the insert 16 is slidably placed on the quick-release lever 14. The desired gauge size indicia 90, 106 are aligned with the detent 44 and nub 42*a*, and the quick-release lever 14 is snapped closed with the insert 16 engaging the guide body 12. The instrument-receiving channel 140 is then formed. Using a proper sterile technique, the unlocked guide body 12 is then coupled to a bracket 80, and lock 18 is moves into the locked position so that guide body 12 is releasably secured to bracket 80. The gauge selection may then be verified. Of course, instrument path verification also should be performed to verify that the desired path has been selected. For example, for a guide 10 attached to an ultrasound probe, a needle disposed in the instrument-receiving channel of the guide should remain in the imaging plane. Guide 10 permits such a needle to both be captured in the imaging pane and released from guide 10 while remaining in the imaging plane. An appropriate instrument length should be selected.

Advantageously, insert 16 may be adjusted once an instrument has been placed in instrument-receiving channel 140 so that a desired feel may be achieved. In addition, in the preferred exemplary embodiment, quick-release lever 14 advantageously permits an instrument guided and captured within instrument-receiving channel 140 to be easily released therefrom by applying downward pressure on front surface 40*a* of support portion 40. Thus, the guide 10 can be "popped" open to easily release an instrument therefrom, and advantageously the instrument may be released without the instrument twisting or rotating in channel 140. Only one hand of the user may be required to manually manipulate guide 10 to release the instrument. Also in the preferred exemplary embodiment, because of the pivotable coupling of the guide body 12 and quick-release lever 14, when these components are in an open position an instrument such as a needle may be inserted or removed sideways from guide 10 (e.g., in a direction along support surface 20 of guide body 12 toward quick-release lever 14). An enhanced visual field is also provided as compared to prior art guides requiring instruments to be removed axially along the instrument-receiving channel thereof.

Advantageously, guide 10 may provide an instrument-receiving channel 140 that has minimal drag when an instrument is disposed therein. Because of the low drag, a user may have enhanced "feel" when positioning an instrument with guide 10 for example during a biopsy procedure. Moreover, guide 10 permits interchangeable inserts to be used so that many different gauges of instruments may be accommodated. Further, instead of only one gauge size being accommodated per insert, the inserts 16, 110 of the present invention each accommodate selection of multiple gauge sizes. Whereas prior art needle guides required ten inserts corresponding to ten different gauge sizes, the present invention for example provides only two inserts that together correspond to ten different gauge sizes. Thus, a wide range of gauge adjustment is possible with a single insert 16, 110, and the number of components to be supplied to the physician may be smaller thereby permitting increases in efficiency and cost-effectiveness. In addition, guide 10 provides ergonomically advantageous features to enhance ease of use, such as regions for manipulating guide 10 with only one or two fingers.

In addition, guide 10 may permit enhanced functionality and control over fixed-angle devices by permitting selection of multiple angles. Optionally, the needle guide may permit placement of more than one needle into a patient at one time, or facilitate multiple placements.

Guide 10 is applicable, for example, in abdominal fine needle aspiration, core biopsy, drainage aspiration, amniocentesis, and catheterization procedures.

Guide 10 may be a single-use, disposable system. Preferably, the components of guide 10 described herein may be formed of injection-molded, ABS polymer. To assist users, each of the components may be color-coded.

Turning to FIGS. 15 and 16, additional exemplary embodiments of instrument guides are shown. Referring first to FIG. 15, a needle guide 210 may include a securing portion 212 and an instrument engaging portion 214. Securing portion 212 is preferably configured to releasably secure needle guide 210 to an imaging transducer. Securing portion 212 may comprise an open clip 215 having first and second ends 216, 218. An angle θ between a line 220 connecting first and second ends 216, 218 and an instrument guide path 222 of instrument engaging portion 214 is preferably less that 45°, for example less than 20°. In one exemplary embodiment, line 220 and guide path 222 are aligned with one another. In one exemplary embodiment, line 220 and guide path 222 are contained within a single plane.

Instrument engaging portion 214 is preferably configured to operatively secure an instrument, such as a biopsy needle, along guide path 222. Engaging portion 214 may comprise first and second engaging portions 224, 226. First engaging portion 224 may include at least one surface 228 preferably shaped to accommodate a portion of an instrument. First engaging portion 224 may include a second surface 229 spaced part along the guide path 222 from surface 228 and preferably shaped to accommodate a portion of the instrument. Second engaging portion 226 preferably includes a surface 230 also preferably shaped to accommodate a portion of the instrument. First and second engaging portions 224, 226 may cooperate to operatively secure the instrument. For example, an instrument may be compressed between (a) surface 230 and (b) surface 228 and, optionally, surface 229. In one exemplary embodiment, surfaces 228-230 contact the instrument in a three-point contact configuration. Preferably, the first and second portions 224, 226 are configured to receive an instrument laterally with respect to the guide path 222. A resilient member or compression spring 239*a* may be provided to bias second engaging portion 226. This spring-loaded arrangement preferably is configured so that movement of second engaging portion 226 in a direction parallel to a central axis of thumb screw 239*b* is resisted, and thus second engaging portion 226 may releasably abut and retain an instrument along guide path 222. A finger depression surface 239*c* may be provided so that pressure applied on surface 239*c* toward thumb screw 239*b* may release an instrument captured along guide path 222.

Engaging portion 214 may be configured to allow motion, for example rotation, of guide path 222. Preferably, guide path 222 may be rotated with respect to securing portion 212. In one embodiment, a rotational motion of guide path 222 is accompanied by a rotational motion of at least one of first and second engaging portions 224, 226 so that an orientation of guide path 222 relative to the first and second engaging portions 224, 226 does not change as guide path 222 is rotated. An example of this may be seen upon comparing FIGS. 15*a* and 15*d*. An arcuate ratcheting mechanism 240 may be provided for angular adjustment and retention of securing portion 212 in pre-set angular positions with respect to engaging portion 214, with securing portion 212 being pivotally connected to engaging portion 214 along axis 242. A pin 241*a* of portion 214, for example, may be received in a plurality of grooves 241*b* formed in ratcheting mechanism 240 of portion 212. Thumb screw 239*b* is provided to apply selectable pressure against an instrument held along axis 242 and thus provides selectable drag on the instrument.

Referring to FIG. 16, yet another embodiment of an instrument guide 210' is shown and may include a securing portion 212' and an instrument engaging portion 214'. Labeled elements of FIG. 16 having similar reference numerals with elements of FIG. 15 and thus may have similar functions with those elements. In particular, a needle guide 210' may include a securing portion 212' and an instrument engaging portion 214'. Securing portion 212' preferably may be configured for use with a bracket to releasably secure needle guide 210', for example, to an imaging transducer. Securing portion 212' may comprise first and second ends 216', 218'. In one exemplary embodiment, an angle between a line 220' connecting first and second ends 216', 218' and an instrument guide path 222' of instrument engaging portion 214' is preferably less that 45°, for example less than 20°. Also in one exemplary embodiment, line 220' and guide path 222' may be aligned with one another. Further, in one exemplary embodiment, line 220' and guide path 222' are contained within a single plane.

Instrument engaging portion 214' is preferably configured to operatively secure an instrument, such as a biopsy needle, along guide path 222'. Engaging portion 214' may comprise first and second engaging portions 224', 226'. First engaging portion 224' may include at least one surface 228' preferably shaped to accommodate a portion of an instrument. First engaging portion 224' may include a second surface 229' spaced part along the guide path 222' from surface 228' and preferably shaped to accommodate a portion of the instrument. Second engaging portion 226' preferably includes a surface 230' also preferably shaped to accommodate a portion of the instrument. First and second engaging potions 224', 226' may cooperate to operatively secure the instrument, for example by forming an instrument receiving chamber. For example, an instrument may be compressed between (a) surface 230' and (b) surface 228' and, optionally, surface 229'. In one exemplary embodiment, surfaces 228'-230' contact the instrument in a three-point contact configuration. Preferably, the first and second portions 224', 226' are configured to receive an instrument laterally with respect to the guide path 222'. A resilient member or torsion spring 239*a'* may be provided to bias second engaging portion 226', which rotates about axis 250 in direction C, toward a position that abuts an instrument releasably retained along guide path 222'. A finger depression surface 239*c'* may be provided so that pressure applied on surface 239*c'* may release or capture an instrument, as desired, along guide path 222.

Engaging portion 214' may be configured to allow motion, for example rotation, of guide path 222'. Preferably, guide path 222' may be rotated with respect to securing portion 212'. In one embodiment, a rotational motion of guide path 222' is accompanied by a rotational motion of at least one of first and second engaging portions 224', 226' so that an orientation of guide path 222' relative to the first and second engaging portions 224', 226' does not change as guide path 222' is rotated. An arcuate ratcheting mechanism 240' may be provided for angular adjustment and retention of securing portion 212' in pre-set angular positions with respect to engaging portion 214', with securing portion 212' being pivotally connected to engaging portion 214' along axis 242'. A protrusion 241*a'* of portion 214', for example, may be received in a plurality of grooves 241*b'* formed in ratcheting mechanism 240' of portion 212'. Thumb screw 239*b'* is provided to apply selectable pressure on surface 239*c'* and consequently selectable pressure of surface 230' against an instrument held along axis 242'. Thus, adjustment knob 239*b'* may provide selectable drag on the instrument.

Advantageously, instrument guides 210, 210' may offer features directed to the benefits of the freehand method while also having the inherently greater control and security of the needle guide method (as these methods were described above). In preferred exemplary embodiments, instrument guides 210, 210' may accept any instrument such as a needle, probe or catheter having a diameter including but not limited to all of the standard sizes of 27 gauge through 8.5 French. Preferably, quick engagement or disengagement of a guide 210, 210' with an instrument may be effected by pressure applied by a finger, while maintaining view of the instrument in the image plane. Also, advantageously the angle of attack for the instrument in the image plane may be user selectable over an angular range by virtue of the arcuate ratcheting mechanisms 240, 240' that also may maintain the chosen angle. In addition, the "dead space" problem may be eliminated by virtue of a curved shoe 252 at the base of the guide. Preferred exemplary embodiments of instrument guides 210, 210' are formed of single use, injection molded parts whose design and related manufacturing costs allow the guides to be cost effective for use.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, guide body 12 and quick-release lever 14 may be formed of unitary construction, with a flexible portion disposed therebetween to permit opening and closing of the device to form instrument-receiving channel 140. Accordingly, all expedient modifications readily attainable by one versed in the art from the disclosure set forth herein that are within the scope and spirit of the present invention are to be included as further embodiments of the present invention.

The scope of the present invention is accordingly defined as set forth in the appended claims.

What is claimed is:

1. A medical instrument guide comprising:
   a guide body having a first support surface;
   a quick-release lever having a support portion, a gauge indicator portion, and a detent; and
   an insert demountably coupled to the quick-release lever and comprising a second support surface and a plurality of notches shaped for selective engagement with the detent, the second support surface being disposed parallel to the first support surface to form an instrument-receiving channel therebetween, said instrument-receiving channel having a central longitudinal axis;
   wherein the selective engagement of the detent with the plurality of notches establishes a plurality of different index positions, each of the index positions corresponding to a different size instrument-receiving channel; and
   wherein the insert is movable along a path extending at an acute angle to the central longitudinal axis to any one of the index positions to move said first support surface relative to the second support surface and thereby change the size of the instrument receiving channel.

2. The medical instrument guide of claim 1, wherein the guide body and quick-release lever are pivotably coupled to each other.

3. The medical instrument guide of claim 2, wherein the guide body comprises a socket and the quick-release lever comprises a post, the post being accommodated in the socket.

4. The medical instrument guide of claim 3, wherein the post demountably snap-fits in the socket.

5. The medical instrument guide of claim 1, wherein the quick-release lever comprises a pair of rails and the insert comprises a pair of insert grooves, with each rail being received in one of the insert grooves.

6. The medical instrument guide of claim 5, wherein the insert further comprises a locking portion extending from a side thereof.

7. The medical instrument guide of claim 1, wherein the instrument-receiving channel defines a plurality of central instrument axes corresponding to each of the indexed sizes, and the insert travels at an angle transverse to the central instrument axes.

8. The medical instrument guide of claim 1, further comprising an indicator visible through a slot in the insert, wherein the indicator and the detent simultaneously index the same size.

9. The medical instrument guide of claim 1, wherein the instrument-receiving channel formed by the guide body and insert accommodates elongate instruments with gauge sizes 16 through 22.

10. The medical instrument guide of claim 1, wherein the quick-release lever and insert are slidably associated with each other.

11. The medical instrument guide of claim 1, wherein the guide body and quick-release lever are integrally formed.

12. The medical instrument guide of claim 1, wherein the instrument-receiving channel comprises a funnel portion.

13. The medical instrument guide of claim 1, further comprising a lock operable between an unlocked position and a locked position, wherein in the locked position a portion of the lock extends into a channel in the guide body.

14. A medical instrument guide comprising:
   a guide body;
   a quick-release lever having a support portion, a gauge indicator portion, and a detent; and
   an insert demountably coupled to the quick-release lever and having a plurality of notches shaped for selective engagement with said detent;
   wherein the guide body and insert are configured and dimensioned to cooperate to form an instrument-receiving channel and the detent is positioned to index a plurality of different sizes of the channel;
   wherein the quick-release lever comprises a pair of rails and the insert comprises a pair of grooves, with each rail being received in one of the insert grooves;
   wherein the insert further comprises a locking portion extending from a side thereof; and
   wherein the locking portion is received in a guide groove in the guide body.

15. The medical instrument guide of claim 14, wherein the locking portion releasably snap-fits in the guide groove.

16. The medical instrument guide of claim 14, wherein the guide body further comprises at least one stop for limiting travel of the locking portion in the guide groove.

17. The medical instrument guide of claim 14, wherein the rails are aligned with the guide groove when the locking portion is received in the guide groove.

18. The medical instrument guide of claim 17, wherein the instrument-receiving channel defines a plurality of central instrument axes corresponding to each of the indexed sizes, and the insert travels at an angle transverse to the central instrument axes.

19. A medical instrument guide comprising:
   a guide body;
   a quick-release lever having a support portion, a gauge indicator portion, and a detent; and
   an insert demountably coupled to the quick-release lever and having a plurality of notches shaped for selective engagement with said detent;
   wherein the detent is positioned to index a plurality of different sizes of the channel;
   wherein the instrument receiving channel formed by the guide body and insert accommodates elongate instruments with gauge sizes 16 through 22 and defines a plurality of central instrument axes corresponding to each of the indexed sizes;
   wherein the insert travels at an angle transverse to the central instrument axes; and
   wherein each of the gauge sizes is indexed by engagement of the detent with a notch.

20. The medical instrument guide of claim 19, wherein the insert further comprises indicia corresponding to the indexed gauge sizes.

21. A medical instrument guide comprising:
   a guide body;
   a quick-release lever having a support portion, a gauge indicator portion, and a detent;
   an insert demountably coupled to the quick-release lever and having a plurality of notches shaped for selective engagement with said detent; and
   wherein the guide body and insert are configured and dimensioned to cooperate to form an instrument-receiving channel and detent is positioned to a plurality of different sizes of the channel; and
   a lock demountably attached to the guide body;
   wherein the instrument receiving channel defines a plurality of central instrument axes corresponding to each of the indexed sizes, and the insert travels at an angle transverse to the central instrument axes.

22. The medical instrument guide of claim 21, wherein the lock and guide body together define an unlocked position and a locked position.

23. The medical instrument guide of claim 22, wherein the lock comprises a protrusion and in the locked position the protrusion extends into a bracket-receiving channel in the guide body.

24. The medical instrument guide of claim 23, further comprising a bracket, wherein the bracket is demountably attachable to the guide body and secured thereto when a portion of the bracket is disposed in the bracket-receiving channel and the lock is disposed in the locked position.

25. The medical instrument guide of claim 24, wherein the bracket is configured and dimensioned to support an ultrasound transducer.

26. A medical instrument guide comprising:
a first portion;
a second portion having a lever, a gauge indicator, and a detent; and
a third portion demountably coupled to the second portion and having a plurality of notches shaped for selective engagement with said detent;
wherein the first and second portions are pivotably associated with each other between an open position and a closed position and vice versa;
wherein the first and third portions are configured and dimensioned to cooperate to form an instrument-receiving channel when said first and second portion are in said closed position;
wherein the detent is arranged to establish a plurality of different index positions, each of said positions establishing a different size of the channel; and
wherein the the third portion is arranged to be moved along a path extending at an acute angle to the central instrument axis to any desired index position to change the size of the instrument-receiving channel.

27. The medical instrument guide of claim 26, wherein the instrument-receiving channel is configured and dimensioned to accommodate a needle.

28. The medical instrument guide of claim 26, wherein the instrument-receiving channel is configured and dimensioned to accommodate a catheter.

29. An instrument guide kit for guiding medical instruments, the kit comprising:
a guide body;
a pair of inserts each releasably engageable with the guide body;
wherein a combination of the guide body and any one of the inserts is configured and dimensioned to form an instrument-receiving channel;
wherein each insert is arranged to be moved along a predetermined path to any one of a plurality of index positions, each of said index positions establishing a different, discrete size of the instrument-receiving channel;
wherein the instrument-receiving channel defines a plurality of central instrument axes corresponding to each of the plurality of discrete sizes; and
wherein said predetermined path extends at an acute angle to the central instrument axes.

30. A guide for use with a medical imaging instrument, the guide comprising:
a first portion;
a second portion proximate the first portion and slidable along a path with respect to the first portion; and
a cavity at least partially formed by the first and second portions, the cavity having a cavity width and configured to retain an elongate instrument therein;
wherein the cavity width is selectively changeable to accommodate a plurality of diameters by sliding the second portion along a said path; and
wherein the cavity defines a plurality of central instrument axes corresponding to each of the plurality of diameters, and said path extends at an acute angle to the central instrument axes.

31. The guide of claim 30, wherein said path is substantially linear.

32. The guide of claim 30, wherein the cavity width is adjustable without rotation of the second portion.

33. The guide of claim 30, wherein the second portion comprises an instrument-contacting surface configured to remain parallel to the central axis.

34. The guide of claim 30, wherein the first and second portions are pivotable with respect to each other and wherein rotation of the second portion permits generally lateral removal of an instrument from the guide without moving the instrument along the central axis.

35. A guide for use with an imaging instrument, the guide comprising:
a first portion configured to engage an elongate instrument;
a second portion configured to cooperate with the first portion and engage the elongate instrument;
an elongate instrument path defined by the cooperation of the first and second portions and arranged to accommodate an instrument therein, the instrument path having a instrument path axis and a diameter;
a track defining a travel axis extending at an acute angle to the instrument path axis, the track configured to engage the second portion while permitting travel of the second portion along the track axis; and
wherein the diameter of the instrument path changes as the second portion travels along the track to accommodate different size elongated instruments within the instrument path.

36. The guide of claim 35, wherein the first and second portions are rotatably associated with each other, and wherein rotation of the portions with respect to each other permits generally lateral removal of the elongate instrument from the guide without moving the elongate instrument along the instrument path axis.

37. The guide of claim 35, wherein the second portion indexes a plurality of discrete elongate instrument diameters to be accommodated along the instrument path.

38. The guide of claim 35, further comprising a bracket configured and dimensioned for coupling to the imaging instrument, wherein the bracket is demountably associated with the first portion.

* * * * *